United States Patent [19]
Trybulski et al.

[11] Patent Number: 4,952,600
[45] Date of Patent: Aug. 28, 1990

[54] 3- OR 4-SUBSTITUTED OXOTREMORINE DERIVATIVES AND A METHOD OF TREATING CENTRAL CHLOINERGIC DSYFUNCTION THEREWITH

[75] Inventors: Eugene J. Trybulski, Bergen, N.J.; Richard H. Kramss, Newburgh; Herbert J. Brabander, Nauet, both of N.Y.

[73] Assignee: American Cyanamid Company, Wayne, N.J.

[21] Appl. No.: 481,924

[22] Filed: Feb. 20, 1990

Related U.S. Application Data

[62] Division of Ser. No. 300,447, Jan. 23, 1989.

[51] Int. Cl.$^5$ ................... C07D 207/12; A61K 31/40
[52] U.S. Cl. ..................................... 514/424; 514/428; 548/541; 548/556

[58] Field of Search ............... 548/556, 541; 514/424, 514/428

[56] References Cited

U.S. PATENT DOCUMENTS

| | | | |
|---|---|---|---|
| 4,243,672 | 1/1981 | Barnish et al. | 514/424 |
| 4,536,500 | 8/1985 | Bourgery et al. | 514/428 |
| 4,847,284 | 7/1989 | Schwartz et al. | 514/424 |

Primary Examiner—David B. Springer
Attorney, Agent, or Firm—Kenneth J. Dow

[57] ABSTRACT

This disclosure describes novel 3 or 4 substituted oxotremorine derivatives having polar substituted oxygen or sulfur groups. The compounds have cholinergic activity. Also disclosed are methods for treating diseases of the central nervous system in mammals employing the compounds, pharmaceutical preparations containing the compounds and processes for the production of the compounds.

7 Claims, No Drawings

3- OR 4-SUBSTITUTED OXOTREMORINE DERIVATIVES AND A METHOD OF TREATING CENTRAL CHLOINERGIC DSYFUNCTION THEREWITH

This is a divisional of co-pending application Ser. No. 300,447, filed on Jan. 23, 1989.

SUMMARY OF THE INVENTION

This invention is concerned with new compounds described by the following formulae I, II, III, IV and V, which have cholinergic activity; with methods for treating diseases of the central nervous system in mammals employing these new compounds; with pharmaceutical preparations containing these compounds; and with processes for the production of these compounds.

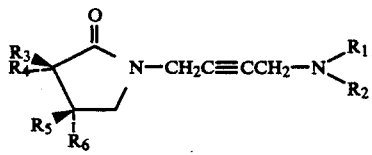

Formula I

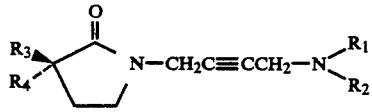

Formula II

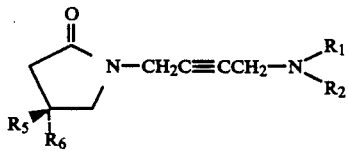

Formula III

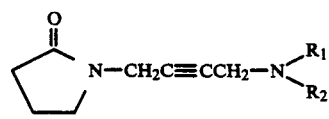

Formula IV

In formulae I, II, III, IV and V, $R_1$ and $R_2$ are each independently selected from the group consisting of ($C_1$-$C_6$) straight or branched chain alkyl groups and moieties of the formula:

wherein $R_1$ and $R_2$ taken together with their associated N(itrogen) are selected from the group consisting of azetidine, aziridine, pyrrolidine, piperidine and

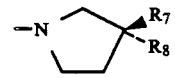

where $R_7$ and $R_8$ are independently selected from the group consisting of ($C_1$-$C_6$)acyloxy, ($C_1$-$C_6$)alkoxy, aroyloxy, substituted aroyloxy, hydroxy, thio, ($C_1$-$C_6$)alkylthio, ($C_1$-$C_6$)alkyldithio, acylthio and hydrogen with the proviso that one of $R_7$ and $R_8$ must be hydrogen; $R_3$, $R_4$, $R_5$, and $R_6$, are selected from the group consisting of hydrogen, hydroxy, ($C_1$-$C_6$)acyloxy, aroyloxy, substituted aroyloxy, ($C_1$-$C_6$)alkoxy, thio, ($C_1$-$C_6$)alkylthio, ($C_1$-$C_6$)alkyldithio, ($C_1$-$C_6$)acylthio and alkylsilyloxy with the proviso that at least one of $R_3$, $R_4$, $R_5$, $R_6$, $R_7$ and $R_8$ must be taken from the group consisting of hydroxy, ($C_1$-$C_6$)acyloxy, aroyloxy, substituted aroyloxy, ($C_1$-$C_6$)alkoxy, thio, ($C_1$-$C_6$)alkylthio, ($C_1$-$C_6$)alkyldithio, ($C_1$-$C_6$)acylthio and alkylsilyloxy; and the pharmacologically acceptable salts thereof.

In addition this invention is concerned with the oxidative dimers of Formulae I, II and III wherein any two of $R_3$ through $R_8$ may be thio as illustrated by the compound [R-(R*,R*)]-3,3'-dithiobis[1-[4-(1-piperidinyl)-2-butynyl]]-2-pyrrolidinone, having the structure:

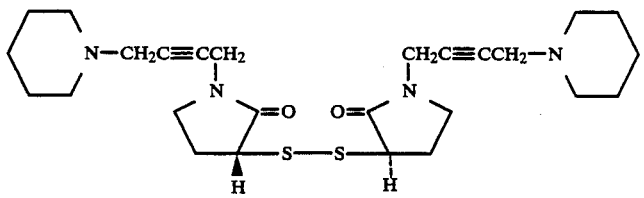

Formula V

DESCRIPTION OF THE INVENTION

The novel compounds of the present invention may be readily prepared in accordance with one or more of the following reaction schemes:

Scheme I

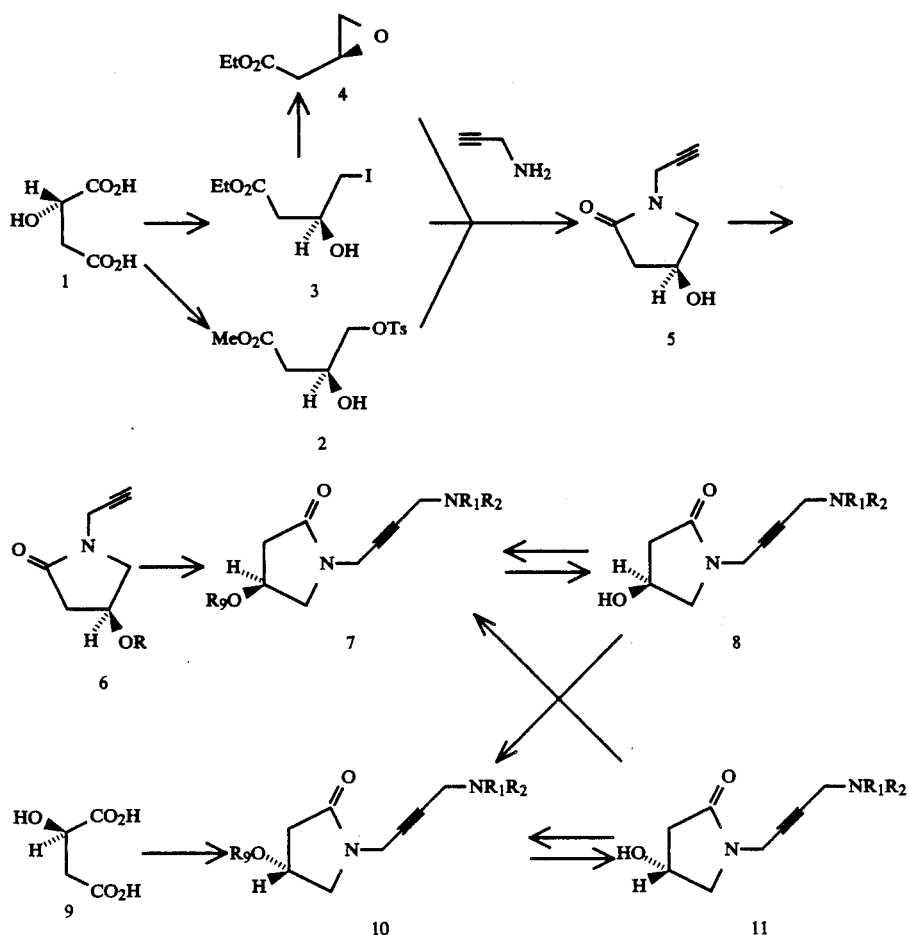

SCHEME I

In accordance with Scheme I, (S)-3-hydroxy-4-[[(4-methylphenyl)sulfonyl]oxy]butanoic acid methyl ester 2, (S)-3-hydroxy-4-iodobutanoic acid ethyl ester 3 and (S)-oxiraneacetic acid ethyl ester 4 are prepared from (S)-malic acid 1 using previously described methods [S. Saito et. al. Chem. Lett. 1389, (1984) and M. Larcheveque et. al. Tetrahedron Lett. 1781, 28 (1987)]. The esters 2, 3 and 4 are individually reacted with propargylamine in an alcohol solvent at temperatures ranging from room temperature to the reflux temperature of the solvent, preferably in the presence of an alkali metal carbonate, to produce (S)-4-hyroxy-1-(2-propynyl)-2-pyrrolidinone 5. Compound 5 is then reacted with an aryl or a ($C_1$–$C_6$) carboxylic acid anhydride such as acetic anhydride in the presence of pyridine and preferably dimethylaminopyridine in an ether or a chlorohydrocarbon solvent, such as dichloromethane, to give the intermediate of general formula 6, for example, (S)-4-(acetyloxy)-1-(2-propynyl)-2-pyrrolidinone.

The compound of general formula 6 is reacted with paraformaldehyde, acetic acid, copper (I) or (II) chloride and a secondary amine such a pyrrolidine in a ethereal solvent such as dioxane in an inert atmosphere at the reflux temperature of the solvent of give, on basification, the pyrrolidinone of general formula 7. The compound of general formula 7 is reacted with an alkali metal carbonate or hydroxide in an alcohol solvent at or around room temperature to produce a compound of general formula 8.

In an analogous fashion to the preparation of compounds of general formulas 7 and 8 from (S)-malic acid 1, compounds of general formulas 10 and 11 are prepared from (R)-malic acid 9.

Reaction of a compound of general formula 8 with an aryl or a ($C_1$–$C_6$) carboxylic acid, a trialkyl or triarylphosphine and a dialkyl or a diarylalkyl azodicarboxylate in an ether or chlorohydrocarbon solvent at or around 0° C. affords the compound of general formula 10.

Reaction of a compound of general formula 11 with a ($C_1$–$C_6$) carboxylic acid, a trialkyl of triarylphosphine and a dialkyl or diarylalkyl azodicarboxylate in an ether or a chlorohydrocarbon solvent at or around 0° C. affords the compounds of general formula 7.

Scheme II

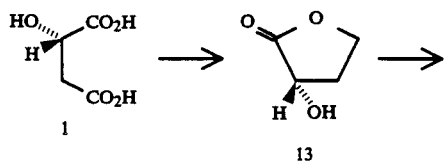

-continued
Scheme II

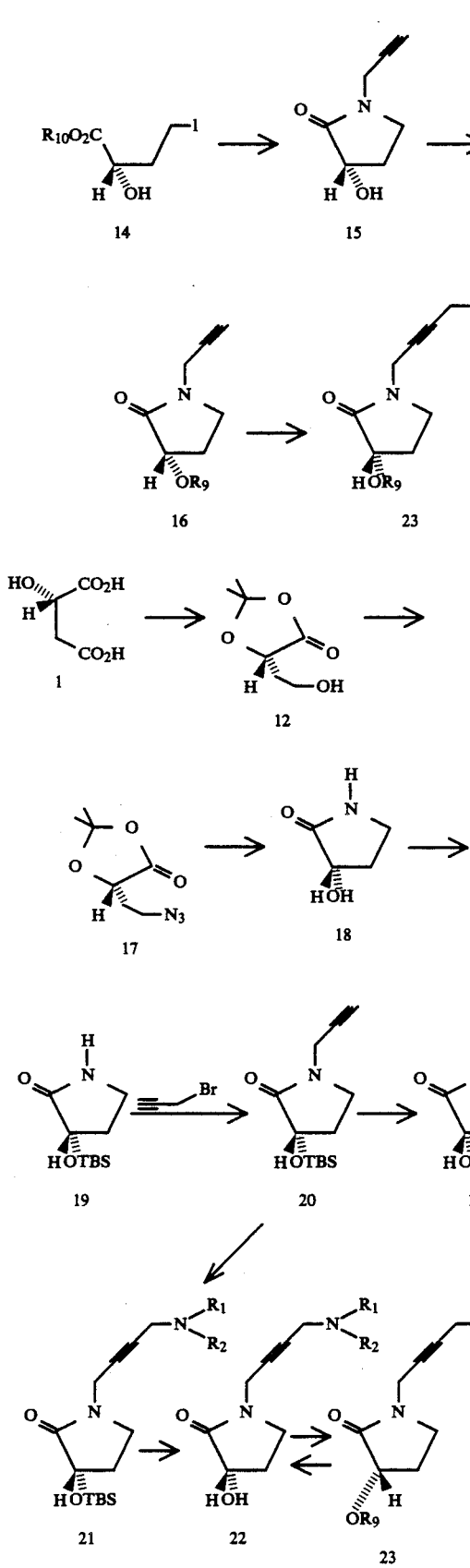

-continued
Scheme II

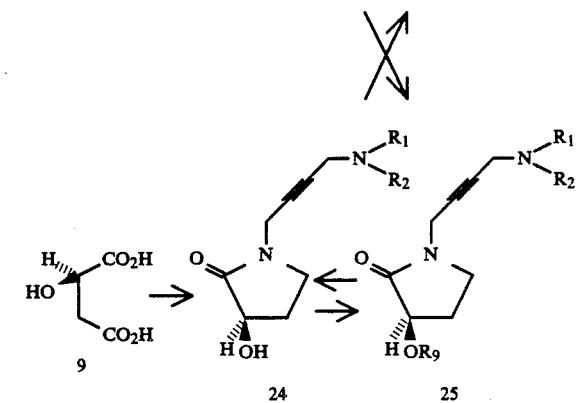

SCHEME II

In accordance with Scheme II, (S)-2,2-dimethyl-4-(2-hydroxymethyl)-5-oxo-1,3-dioxolane 12 and (S)-dihydro-3-hydroxy-2(3H)-furanone 13 are prepared using previously described methods [D. B. Collum et. al. J. Amer. Chem. Soc. 2118, 102, (1980)] from (S)-malic acid 1. The furanone 13 is reacted with iodotrimethylsilane in an alcohol solvent at a temperature ranging from 0° C. to the reflux temperature of the solvent, with room temperature preferred, to give the ester of general formula 14, where $R_{10}$ is a ($C_1$-$C_6$) straight or branched chain alkyl. The compound of general formula 14 is reacted with propargylamine in an alcohol solvent at a temperature ranging from room temperature to the reflux temperature of the solvent, preferably in the presence of an alkali metal carbonate, to produce (S)-3-hydroxy-1-(2-propynyl)-2-pyrrolidinone 15. Compound 15 is then reacted with an aryl or a ($C_1$-$C_6$) carboxylic acid, such as acetic anhydride, in the presence of pyridine and preferably in the presence of dimethylaminopyridine in an ether or chlorohydrocarbon solvent, such as dichloromethane, to give the intermediate of general formula 16, where $R_9$ is

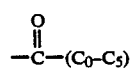

straight or branched chain alkyl or

or substituted aryl, for example (S)-3-acetoxy-1-(2-propynyl)-2-pyrrolidinone.

In a second and complementary manner, compound 15 is prepared from furanone 12. Reaction of acetonide 12 with hydrazoic acid, a trialkyl or a triarylphosphine and a dialkyl azodicarboxylate in an ether or chlorohydrocarbon solvent, such as dichloromethane, at or around 0° C. affords the compound of formula 17. Reaction of compound 17 with hydrogen gas in an ether or alcohol solvent in the presence of platinium oxide at or around room temperature gives (S)-3-hydroxy-2-pyrrolidinone 18. Reaction of compound 18 with a greater than two fold excess of tert-butyldimethylsilyl chloride and a tertiary amine base, such as triethylamine, in a ether or chlorohydrocarbon solvent at or around room temperature followed by a reflux period of between 1 to 12 hours in methanol produces compound 19. Treatment of compound 19 with a strong base, such as sodium hydride or potassium tert-butoxide, in an ether solvent at or around 0° C. followed by the addition of propargyl bromide gives compound 20. Reaction of compound 20 with alcoholic hydrogen chloride affords compound 15.

A compound of general formula 16 is reacted with paraformaldehyde, acetic acid, copper (I) or (II) chloride and a secondary amine, such as pyrrolidine, in an ether solvent, such as dioxane, under an inert atmosphere at reflux to give on basification a compound of general fomula 23.

A compound of formula 20 is reacted with paraformaldehyde, acetic acid, copper (I) or (II) chloride and a secondary amine, such as pyrrolidine, in an ether solvent, such as dioxane, under an inert atmosphere at reflux to give on basification a compound of general formula 21. Reaction of a compound of general formula 21 with alcoholic hydrogen chloride affords a compound of general formula 22. A compound of general formula 22 is then reacted with an aryl or a ($C_1$–$C_6$) carboxylic acid, such as acetic anhydride, in the presence of pyridine and preferrably in the presence of dimethylaminopyridine in an ether or chlorohydrocarbon solvent, such as dichloromethane, to give a compound of general formula 23.

A compound of general formula 23 is reacted with an alkali metal carbonate or hydroxide in a alcohol solvent at or around room temperature to produce a compound of general formula 22.

In an analogous fashion to the preparation of compounds of general formulas 22 and 23 from (S)-malic acid 1, compounds of general formulas 24 and 25 are prepared from (R)-malic acid 9.

Reaction of a compound of general formula 22 with an aryl or a ($C_1$–$C_6$) carboxylic acid, a trialkyl or triarylphosphine and a dialkyl or an diarylalkyl azodicarboxylate in an ether or a chlorohydrocarbon solvent at or around 0° C. affords a compound of general formula 25.

Reaction of a compound of general formula 24 with an aryl or a ($C_1$–$C_6$) carboxylic acid, a trialkyl or triarylphosphine and a dialkyl or diarylalkyl azodicarboxylate in an ether or a chlorohydrocarbon solvent at or around 0° C. affords a compound of general formula 23.

A compound of general formula 25 is reacted with an alkali metal carbonate or hydroxide in an alcohol solvent at or around room temperature to produce a compound of general formula 24.

Scheme III

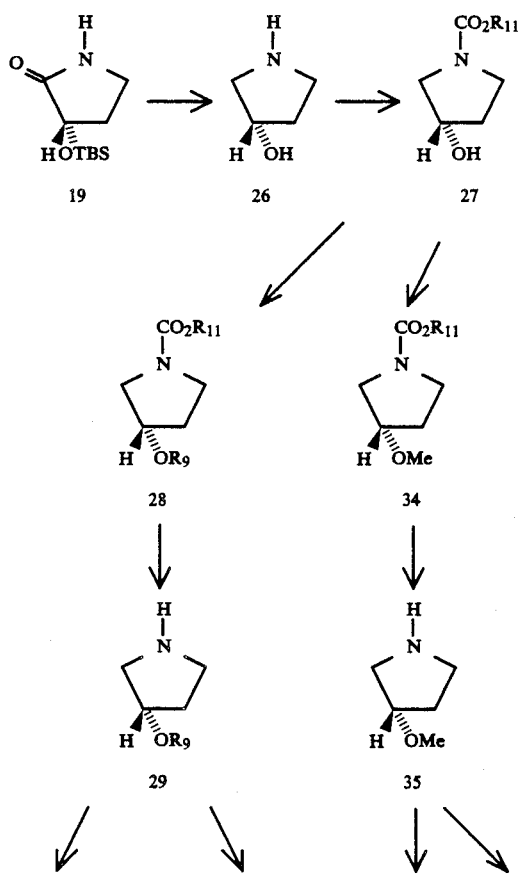

Scheme III

-continued

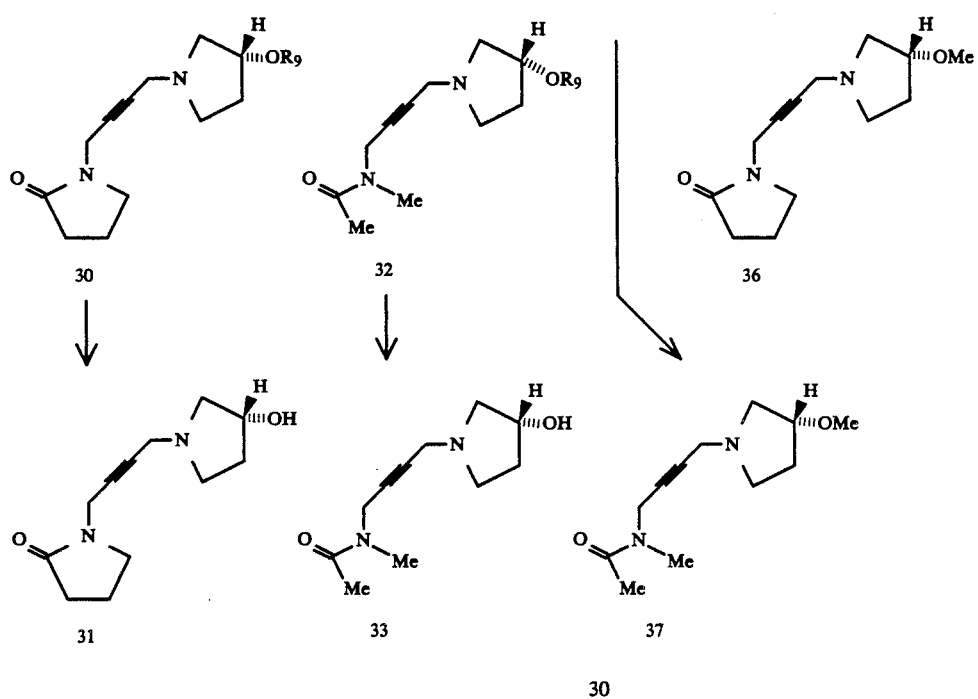

According to Scheme III a compound of the formula 19 is reacted with a metal hydride reducing agent such as lithium aluminum hydride at or around 0° C. to produce (S)-3-pyrrolidinol 26. A number of alternate synthetic procedures are available for the synthesis of compound 26 in the optically active (S)-form, the (R)-form (compound 38), as well as the racemic form [D. Flanagan et. al. Heterocycles 2247, 26, (1987) M. Hashimoto, Chem. Lett. 893 (1986)]. In addition, the racemic form of the compound is commercially available. Reaction of compound 26, using the published procedure [B. Harris et. al. Synth. Commun., 1815, 16, (1986)] affords a compound of general formula 27, where $R_{11}$ is a substituted phenylmethyl. Reaction of a compound of general formula 27 with an aryl or a ($C_1$–$C_6$) carboxylic acid anhydride in the presence of pyridine and preferably in the presence of dimethylaminopyridine in an ether or a chlorohydrocarbon solvent at or around 0° C. gives a compound of general formula 28. Reduction of a compound of general formula 28 with hydrogen using platinium oxide as catalyst in an ether or alcohol solvent at or around room temperature produces a compound general formula 29.

Reaction of a compound of general formula 29 with paraformaldehyde, acetic acid, copper (I) or (II) chloride and propargylpyrrolidinone in an ether solvent, such as dioxane, under an inert atmosphere and at the reflux temperature of the solvent gives on basification of the reaction medium the compound of general formula 30. Treatment of a compound of general formula 30 with an alkali metal carbonate or hydroxide in an alcohol solvent at or around room temperature gives a compound of general formula 31.

Reaction of a compound of general formula 29 with paraformaldehyde, acetic acid, copper (I) or (II) chloride and N-methyl-N-propargylacetamide in an ether solvent, such as dioxane, under an inert atmosphere and at the reflux temperature of the solvent gives, on basification of the reaction medium, a compound of general formula 32. Treatment of a compound of general formula 32 with an alkali metal carbonate or hydroxide in an alcohol solvent at or around room temperature gives a compound of general formula 33.

Reaction of a compound of general formula 27 with a ($C_1$–$C_6$) alkyl iodide, for example methyl iodide, in the presence of silver (I) oxide in an ether solvent gives a compound of general formula 34. Reduction of a compound of general formula 34 with hydrogen using platinum oxide as catalyst in an ether or alcohol solvent at or around room temperature produces a compound of general formula 35.

Reaction of a compound of general formula 35 with paraformaldehyde, acetic acid, copper (I) or (II) chloride and propargylpyrrolidinone in a ether solvent, such as dioxane, under an inert atmosphere and at the reflux temperature of the solvent gives, on basification of the reaction medium, a compound of general formula 36.

Reaction of a compound of general formula 35 with paraformaldehyde, acetic acid, copper (I) or (II) chloride and N-methyl-N-propargylacetamide in an ether solvent, such as dioxane, under an inert atmosphere and at the reflux temperature of the solvent gives, on basification of the reaction medium, a compound of general formula 37.

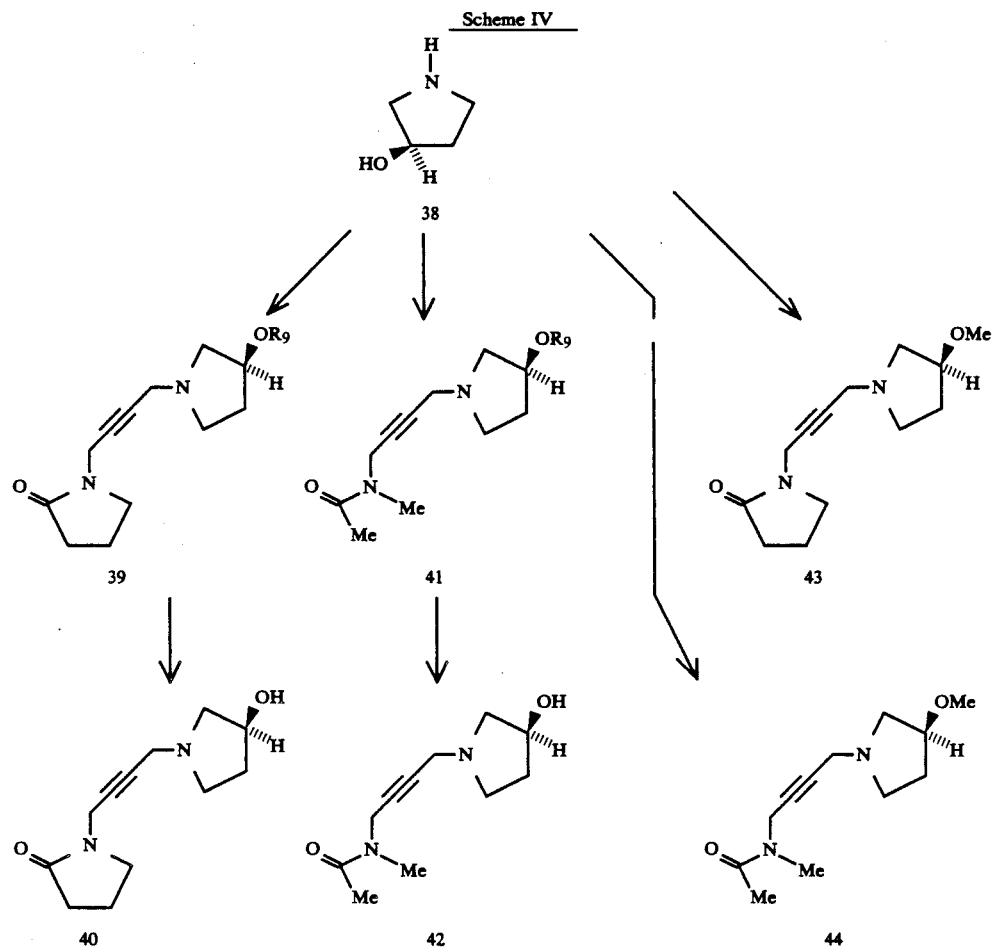
SCHEME IV
In an analogous manner to the preparation of compounds of general formulas 30 to 37 from compound 26, the compounds of general formulas 39 to 44 are prepared (Scheme IV) from (R)-pyrrolidinol 38.
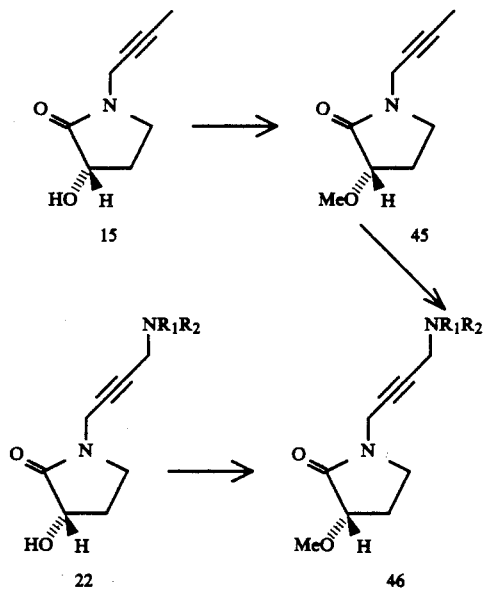

Scheme VI

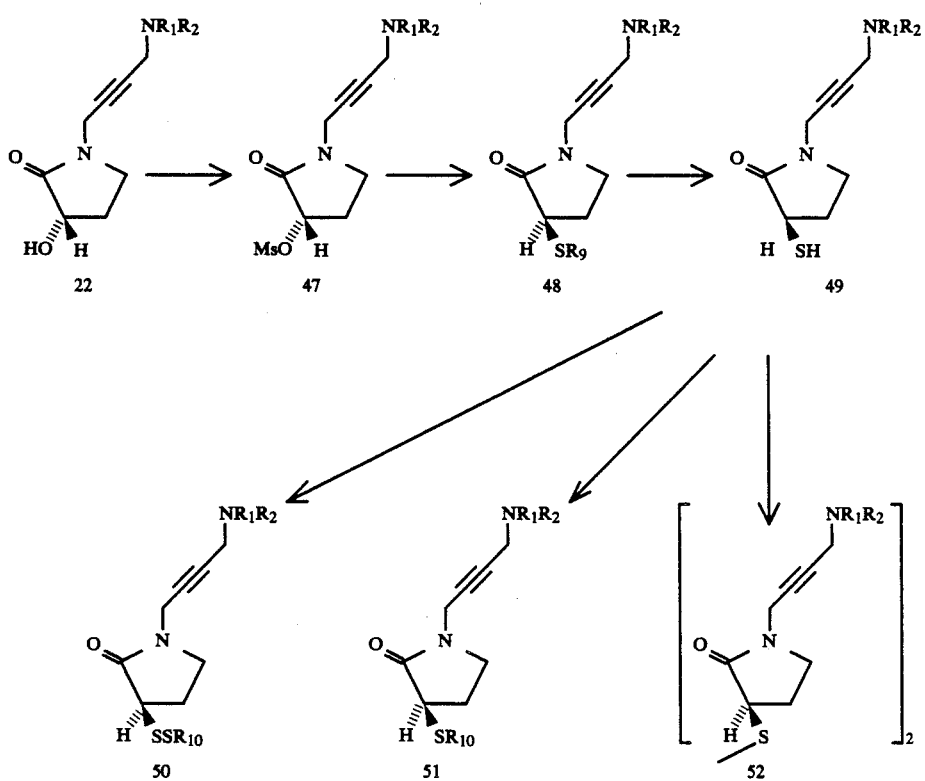

SCHEME V

According to Scheme V, the compound of formula 15 is reacted with diazomethane in an ether solvent or a chlorohydrocarbon solvent at or around 0° C. to give the compound of formula 45. Reaction of the compound of formula 45 with paraformaldehyde, acetic acid, copper (I) or (II) chloride and a secondary amine such as pyrrolidine in a ether solvent, such as dioxane, under an inert atmosphere and at the reflux temperature of the solvent gives on basification of the reaction medium, the compound of general formula 46. Alternately, the reaction of the compound of general formula 22 with diazomethane in an ether solvent or a chlorohydrocarbon solvent at or around 0° C. produces the compound of general formula 46.

SCHEME VI

According to Scheme VI, the compound of general formula 22 is reacted with an alkyl or arylsulfonyl chloride in the presence of an amine base, such as pyridine or triethylamine, in an ether or chlorohydrocarbon solvent at or around 0° C. to produce the compound of general formula 47. Treatment of compound 47 with the alkali metal salt of a ($C_1$–$C_6$) thiocarboxylic acid in an alcohol solvent at or around room temperature affords a compound of general formula 48. Reaction of a compound of general formula 48 with dry hydrogen chloride in an alcohol solvent produces a compound of general formula 49.

Reaction of a compound of general formula 49 with an alkylthiosulfonate in an ether or chlorohydrocarbon solvent at or around room temperature affords a compound of general formula 50.

Reaction of a compound of general formula 49 with a excess of 2-pyridyldisulfide in an ether solvent at or below 0° C. followed by the addition of the required alkyl lithium reagent gives a compound of general formula 51.

Reaction of a compound of general formula 49 with a mild oxidant such as 2-pyridyl disulfide or dimethyl sulfoxide in chlorohydrocarbon solvent at or around room temperature produces a compound of general formula 52.

The present invention relates to compounds, pharmaceutical compositions and to the use of the compounds for the manufacture of pharmaceuticals.

The novel compounds described herein are useful as cholinergic agents. A chronic deficiency in central cholineric function has been implicated in a variety of neurologic and psychiatric disorders, including senile dementia of the Alzheimer's type (SDAT), tardive dyskinesia, Pick's disease and Huntington's chorea. Post mortem neurochemical investigations of patients with SDAT have demonstrated a reduction in presynaptic markers for acetylcholine-utilizing neurons in the hippocampus and the cerebral cortex. [P. Davies and A. J. R. Maloney, Lancet, 1976-II, 1403, (1976); E. K. Perry, R. H. Perry, G. Blessed, B. E. Tomlinson, J. Neurol. Sci., 34, 247, (1976)]. The basis for this cholinergic abnormality is unclear, but evidence suggests that the cholinergic neurons in the neucleus basalis of Meynert may selectively degenerate in SDAT [J. T. Coyle, D. J. Price, M. R. DeLong, Science, 219, 1184, (1983)]. If this degeneration plays a role in behavior symptoms of the disease, then a possible treatment strategy would be to compensate for the loss of cholinergic output to the cortex and hippocampus.

In an aged monkey animal model, designed to mimic the symptoms of SDAT, the direct muscarinic agonists arecoline [R. T. Bartus, R. L. Dean, B. Beer, Neurobiology of Aging, 1, 145, (1980)] and oxotremorine [R. T. Bartus, R. L. Dean, B. Beer, Psychopharmacology Bulletin, 19, 168, (1983)] produced significant improvement in performance. These results in aged monkeys were corroborated in SDAT patients with arecoline which produced a more-consistent improvement when compared to the anticholinesterase inhibitor physostigmine [J. E. Christie, A. Shering, J. Ferguson, A. M. Glen, British Journal of Psychiatry, 138, 46, (1981)].

These animal behavioral and clinical results have instigated significant efforts in a search for a muscarinic agonist which will selectively compensate for the loss of cholinergic input in the hippocampus and cereberal cortex. However, the search must be refined to seek agonists which will not effect significantly the remaining body cholinergic functions. The recent disclosure (T. I. Bonner, N. J. Buckley, A. C. Young, M. R. Brann, Science, 237,527, (1987)] that muscarinic receptors are not all the same but exist as a heterogenous population of receptors substantiates the possibility for the discovery of a selective muscarinic agonist.

The methodical methylation of the muscarinic agonist oxotremorine and its derivatives have been studied in the search for a selective muscarinic agonist [B. Ringhahl, J. Med. Chem. 31, 683, (1988) and references cited within]. The methodical substitution of a methyl group onto oxotremorine can probe the steric nonpolar environment of the muscarinic agonist for its neurotransmitter-receptor-complex.

The present invention describes the preparation of novel oxotremorine derivatives having polar substituted oxygen and substituted sulfur groups. This series of compounds goes beyond the initial study performed by Ringhahl. In an effort to obtain a selective muscarinic agonist, the substitution of oxygen and sulfur groups on the oxotremorine molecule enables one to use the compounds to explore the steric environment of the muscarinic agonist for its neurotransmitter complex. This modification of the oxotremorine molecule is also useful in probing possible auxiliary polar interactions with one of the muscarinic receptors. As such, one or more of the compounds described herein may show selective muscarinic agonist activity. In addition, the polar substituted oxygen and substituted sulfur groups provide a possible point of attachment for drug- delivery auxiliary groups, which could be used to enhance transport of the compound to the active site.

The compounds of this invention were tested for cholinergic activity according to the following procedures.

[$^3$H] Quinuclidinyl Benzilate Binding Assay

This assay is utilized in conjunction with the $^3$H-Cis-methyldioxolane binding assay to evaluate antagonist and high affinity agonist binding properties of CNS cholinergic agents. The procedure was adapted from Watson, M., Yamamura, H. I., and Roeske, W. R., J. Pharmacol. Exp. Ther. 237: 411-418 (1986) and Watson, M., Roeske, W. R., and Yamamura, H. I., J. Pharmacol. Exp. Ther. 237: 419-427 (1986).

Tissue Preparation

Rats are sacrificed by decapitation and the brain removed and placed on ice. The cerebral cortex is dissected on a cold stage, weighed and homogenized (Polytron, setting 5.5 with PT-10 saw-tooth generator for 15 seconds) in 50 volumes (wet wt/vol) of ice-cold 10 mM (8.1 mM Na$_2$HPO$_4$, 1.9 mM KH$_2$PO$_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:3000 (original wet wt/vol) with ice-cold NaKPB for use in the assay. The final protein content per 2.0 ml of incubation mixture is 0.1 mg.

Dilution of Compounds

A stock solution of Atropine is prepared at 0.2 mM to define non-specific binding (1 μM final conc). Test compounds are prepared at 40 mM (final conc 1 mM) in buffer (if water soluble) or in absolute ethanol - 1N HCl (1:1, v/v) and serially diluted to the desired concentrations. In general, dose-response profiles are examined between 1 mM and 1 pM final concentrations.

Preparation of $^3$H-QNB $^3$H-QNB (NEN, NET-656; specific activity=30.0 Ci/mmol) is diluted to 5 nM, with NaPB (final concentration=0.25 nM activity~18,000 cpm at a counting efficiency of 55%).

$^3$H-QNB Binding Assay

A typical protocol is outlined below:

| Tube No. | ID* | Buffer μL | Atropine μL | Test Compound μL | $^3$H-QNB μL | Tissue ml |
|---|---|---|---|---|---|---|
| 1-2 | Total | 50 | — | — | 100 | 1.85 |
| 3-4 | NS | 40 | 10 | — | " | " |
| 5-6 | 4e-11 | — | — | 50 | " | " |
| 7-8 | 4e-10 | — | — | " | " | " |
| 9-10 | 4e-09 | — | — | " | " | " |
| 11-12 | 4e-08 | — | — | " | " | " |
| 13-14 | 4e-07 | — | — | " | " | " |
| 15-16 | 4e-06 | — | — | " | " | " |
| 17-18 | 4e-05 | — | — | " | " | " |
| 19-20 | 4e-04 | — | — | " | " | " |
| 21-22 | 4e-03 | — | — | " | " | " |
| 23-24 | 4e-02 | — | — | " | " | " |

*Stock concentration [M] of compound to be tested.

Components are added in the following order: test compound, radioligand, buffer or tissue to give a final volume of 2.0 ml. After adding the tissue homogenate, the tubes are thoroughly mixed and incubated at 25° C. for 120 minutes. At the end of 120 minutes, the samples are filtered through GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total - NS (non-specific). The percent inhibition of specific binding is then calculated and the IC50 values computed using either the LIGAND or LUNDON software packages for competition binding. The results of this test on representative compounds of this invention appear in Table I.

[$^3$H]-Cis-methyldioxolane Binding Assay (High Affinity)

This assay is utilized in conjunction with $^3$H-QNB binding to evaluate high affinity agonist binding and antagonist properties of CNS cholinergic agents. The procedure was adapted from Vickroy, T. W., Roeske, W. R., and Yamamura, H. I., J. Pharmacol. Exp. Ther.

229: 747–755 (1984). This is a rapid filtration assay that is set up to label only the high affinity agonist conformation of the muscarinic cholinergic receptor.

Tissue Preparation:

Rats are sacrificed by decapitation and the brain removed and placed on ice. The cerebral cortex is dissected on a cold stage, weighed and homogenized (Polytron, setting 5.5 with Pt-10 saw-tooth generator for 15 seconds in 50 volumes (wet wt/vol) of ice-cold 10 mM (8.1 mM $Na_2HPO_4$, 1.9 mM $KH_2PO_4$) sodium-potassium phosphate buffer (NaKPB), pH 7.4. The homogenate is placed in an ice bath for 30 seconds and homogenized again as above. This procedure is repeated once again for a total of three times. The resulting homogenate is then diluted 1:300 (orginal wet wt/vol) with ice-cold NaKPB for use in the assay. The final protein content per 2.0 ml of incubation mixture is 0.75 mg.

Dilution of Compounds:

A stock solution of Atropine is prepared at 0.2 mM to define non-specific binding 1 μM final conc). Test compounds are prepared at 40 mM (final conc 1 mM) in buffer (if water soluble) or in absolute ethanol - 1N HCl (1:1, v/v) and serially diluted to the desired concentrations. In general, dose-response profiles are examined between 1 mM and 1 pM final concentrations.

Preparation of $^3$H-CD:

$^3$H-CD (NEN, NET-647; specific activity=55.5 Ci/mmol) is diluted to 20 nM with NaPB (final conc=1.0 nM, activity~75,000 cpm at a counting efficiency of 55%).

Technical Notes:

$^3$H-CD adheres readily to both glass and plastic surfaces. To eliminate this problem (and the chance for introducing artifacts into the results), stock vials, pipette tips and all glass tubes are routinely treated with Prosil-28, a siliconizing agent, and oven dried prior to use in an assay. Additionally, the GF/B glass fiber filters are pre-soaked in an aqueous polyethylenimine (PEI) solution (0.1%, pH 7.0) prior to use.

All points in the inhibition curve (including total and non-specific binding) are always measured on single PEI treated filter strips to minimize filter-to-filter variability. (See Bruns, R. F., et al. Anal. Biochem. 132: 74–81 (1983) for the use of PEI treated filters in filtration receptor assays).

The $^3$H-CD is prepared fresh in buffer just prior to use in the assay to avoid possible decomposition. It should be kept on an ice bath after dilution in buffer.

$^3$H-CD Binding Assay:

A typical protocol is outlined below:

| Tube No. | ID* | Buffer μL | Atropine μL | Test Compound μL | $^3$H-CD μL | Tissue ml |
|---|---|---|---|---|---|---|
| 1–2 | Total | 50 | — | — | 100 | 1.85 |
| 3–4 | NS | 40 | 10 | — | " | " |
| 5–6 | 4e-11 | — | — | 50 | " | " |
| 7–8 | 4e-10 | — | — | " | " | " |
| 9–10 | 4e-09 | — | — | " | " | " |
| 11–12 | 4e-08 | — | — | " | " | " |
| 13–14 | 4e-07 | — | — | " | " | " |
| 15–16 | 4e-06 | — | — | " | " | " |
| 17–18 | 4e-05 | — | — | " | " | " |
| 19–20 | 4e-04 | — | — | " | " | " |
| 21–22 | 4e-03 | — | — | " | " | " |
| 23–24 | 4e-02 | — | — | " | " | " |

*Stock concentration [M] of compound to be tested.

Components are added in the following order: compound, radioligand, buffer or tissue to give a final volume of 2.0 ml. After adding the tissue homogenate, the tubes are thoroughly mixed and incubated at 25° C. for 120 minutes. At the end of 120 minutes, the samples are filtered through PEI pretreated GF/B glass fiber filters (Whatman) using a 24 sample cell harvester (Brandel) under a vacuum of 15 mm Hg. The tubes are washed with 5×3 ml ice-cold NaKPB. The filters are then placed in scintillation vials with 10 ml of scintillation cocktail (Beckman HP or HP/B), allowed to stand overnight, shaken and then counted. Specific binding is calculated as Total - NS (non-specific). The percent inhibition of specific binding is then calculated and the IC50 values computed using either the LIGAND or LUNDON sofware packages for competition binding. The results of this test on representative compounds of this invention appear in Table I.

TABLE I

| Compound | $^3$H-QNB IC$_{50}$ μM | $^3$H-CD IC$_{50}$ nM |
|---|---|---|
| (S)-4-(Acetyloxy)-1-[4-(l-pyrrolidinyl)-2-butynyl]-2-pyrrolidinone | 112 | 6107 |
| (S)-4-(Acetyloxy)-1-[4-(1-piperidinyl)-2-butynyl]-2-pyrrolidinone | 159 | 9568 |
| (S)-4-Hydroxy-1-[4-(1-piperidinyl)-2-butynyl]-2-pyrrolidinone | 200 | 36060 |
| (S)-4-(Acetyloxy)-1-[4-(dimethylamino)-2-butynyl]-2-pyrrolidinone | 1354 | 41900 |
| (S)-1-[4-(Dimethylamino)-2-butynyl]-4-hydroxy-2-oxazolidinone | 1512 | 10060 |
| (R)-4-(Acetyloxy)-1-[4-(1-pyrrolidinyl)-2-butynyl]-2-pyrrolidinone | 46 | 914 |
| (R)-4-Hydroxy-1-[4-(1-pyrrolidinyl)-2-butynyl]-2-pyrrolidinone | 52 | 53 |
| (R)-4-(Acetyloxy)-1-[4-(1-piperidinyl)-2-butynyl]-2-pyrrolidinone | 181 | 8081 |
| (R)-4-Hydroxy-1-[4-(1-piperidinyl)-2-butynyl]-2-pyrrolidinone | 166 | 3794 |
| (R)-4-(Acetyloxy)-1-[4-(dimethylamino)-2-butynyl]-2-pyrrolidinone | 1782 | 11540 |
| (R)-1-[4-(Dimethylamino)-2-butynyl]-4-hydroxy-2-pyrrolidinone | 2350 | 578 |
| 1-[4-(Dimethylamino)-2-butynyl]-2-pyrrolidinone | 163 | 44 |
| 1-[4-(1-Piperidinyl)-2-butynyl]-2-pyrrolidinone | 2 | 77 |
| (S)-3-Hydroxy-1-[4-(1-pyrrolidinyl)-2-butynyl]-2-pyrrolidinone | 11 | 9 |
| (S)-3-Methoxy-1-[4-(1-piperidinyl)-2-butynyl]-2-pyrrolidinone | 673 | 33110 |
| (S)-3-Methoxy-1-[4-(1-pyrrolidinyl)-2-butynyl]-2-pyrrolidinone | 433 | 1166 |
| (S)-3-(Acetyloxy)-1-[4-1-(1-pyrrolidinyl)-2-butynyl]-2-pyrrolidinone | 122 | 152 |
| (R)-3-[(4-Nitrobenzoyl)oxy]-1-[4-(1-pyrrolidinyl)-2-butynyl]-2-pyrrolidinone | 59 | 4287 |
| (R)-3-Hydroxy-1-[4-(1-pyrrolidinyl)-2-butynyl]-2-pyrrolidinone | 47 | 134 |
| (R)-3-(Acetyloxy)-1-[4-(1-pyrrolidinyl)-2-butynyl]-2-pyrrolidinone | 231 | 547 |
| (S)-1-[4-(Dimethylamino)-2-butynyl]-3-[[(1,1-dimethylethyl)dimethylsilyl]oxy]-2-pyrrolidinone | 200 | 19530 |
| (S)-3-(Acetyloxy)-1-[4-(dimethylamino)-2-butynyl] -2-pyrrolidinone | 1357 | 521 |
| (S)-3-[[(1,1-Dimethylethyl)dimethylsilyl]-oxy]-1-[4-(1-piperidinyl)-2-butynyl]-2-pyrrolidinone | 24 | 161 |
| (S)-3-Hydroxy-1-[4-(1-piperidinyl)-2-butynyl]-2-pyrrolidinone | 22 | 476 |
| (S)-3-[[(Methylamino)carbonyl]oxy]-1-[4-(1-piperidinyl)-2-butynyl]-2-pyrrolidinone | 744 | 86970 |
| (S)-3-(Acetyloxy)-1-[4-(1-piperidinyl)-2-butynyl]-2-pyrrolidinone | 367 | 1449 |
| (S)-1-[4-[3-(Acetyloxy)-1-pyrrolidinyl-2-butynyl]-2-pyrrolidinone | 2315 | 2020 |
| (Racemic)-1-[4-[3-(Acetyloxy)-1-pyrrolidinyl]-2-butynyl]-2-pyrrolidinone | 313 | 1328 |
| (Racemic)-1-[4-(3-Hydroxy-1-pyrrolidinyl)- | 395 | 425 |

TABLE I-continued

| Compound | $^3$H-QNB IC$_{50}$ μM | $^3$H-CD IC$_{50}$ nM |
|---|---|---|
| 2-butynyl]-2-pyrrolidinone | | |
| (S)-4-[[(1,1-Dimethylethyl)dimethylsilyl]oxy]-1-[4-(1-pyrrolidinyl)-2-butynyl]-2-pyrrolidinone | 23 | 9570 |
| (S)-4-Hydroxy-1-[4-(1-pyrrolidinyl)-2-butynyl]-2-pyrrolidinone | 270 | 4905 |
| (Racemic)-1-[4-(3-Methoxy-1-pyrrolidinyl)-2-butynyl]-2-pyrrolidinone | 110 | 1746 |
| (R)-3-Methoxy-1-[4-(1-piperidinyl)-2-butynyl]-2-pyrrolidinone | 459 | 28130 |
| (R)-3-Methoxy-1-[4-(1-pyrrolidinyl)-2-butynyl]-2-pyrrolidinone | 283 | 1970 |
| (R)-3-Hydroxy-1-[4-(1-piperidinyl)-2-butynyl]-2-pyrrolidinone | 84 | 3460 |
| (R)-3-[(4-Nitrobenzoyl)oxy]-1-[4-(1-piperidinyl)-2-butynyl]-2-pyrrolidinone | 43 | 937 |
| (R)-1-[4-(Dimethylamino)-2-butynyl]-3-hydroxy-2-pyrrolidinone | 1468 | 578 |
| (R)-1-[4-(Dimethylamino)-2-butynyl]-3-[(4-nitrobenzoyl)oxy]-2-pyrrolidinone | 113 | 5006 |
| (R)-3-(Acetyloxy)-1-[4-(1-piperidinyl)-2-butynyl]-2-pyrrolidinone | 419 | 4469 |
| (Racemic)-N-[4-(3-Methoxy-1-pyrrolidinyl)-2-butynyl]-N-methyl acetamide | 377 | 1367 |
| (Racemic)-N-[4-(3-(Acetyloxy)-1-pyrrolidinyl]-2-butynyl]-N-methyl acetamide | 1929 | 5459 |
| (Racemic)-N-[4-(3-Hydroxy-1-pyrrolidinyl)-2-butynyl]-N-methyl acetamide | 1189 | 2010 |
| N,N,N-Trimethyl-4-(2-oxo-1-pyrrolidinyl)-2-butyn-1-aminium iodide | 18 | 3 |
| (S)-4-(3-Hydroxy-2-oxo-1-pyrroidinyl)-N,N,N-trimethyl-2-butyn-1-aminium | 72 | 14 |
| [R-(R*,R*)]-3,3-Dithiobis-[1-[4-(1-piperidinyl)-2-butynyl]]-2-pyrrolidinone | 9 | 1835 |
| (R)-S-[2-Oxo-1-(4-piperidinyl-2-butynyl)-3-pyrrolidinyl]ethanethioic acid ester | 91 | 946 |
| 3-Mercapto-1-[4-(1-piperidinyl)-2-butyn-yl]-2-pyrrolidinone | 11 | 587 |
| (S)-S-[1-[4-(Dimethylamino)-2-butynyl]-2-oxo-3-pyrrolidinyl]ethanethioic acid ester | 40 | 1533 |
| (S)-S-[2-Oxo-1-[4-(1-piperidinyl)-2-butynyl]-3-pyrrolidinyl]ethanethioic acid ester | 14 | 2428 |
| (S)-3-Mercapto-1-[4-(1-piperidinyl)-2-butynyl]-2-pyrrolidinone, monohydrochloride | 2.5 | 955 |
| (R)-S-[2-Oxo-1-[4-(1-piperidinyl)-2-butynyl]-3-pyrrolidinyl]ethanthioic acid ester | 4.3 | 30 |
| (R)-3-Mercapto-1-[4-(1-pyrrolidinyl)-2-butynyl]-2-oxazolidinone, monohydrochloride | 1 | 7 |
| (R)-S-[1-[4-(Dimethylamino)-2-butynyl]-2-oxo-3-pyrrolidinyl]ethanethioic acid ester | 20 | 62 |
| (R)-1-[4-(Dimethylamino)-2-butynyl]-3-mercapto-2-pyrrolidinone, monohydrochloride | 31 | 76 |
| (S)-S-(2-Oxo-1-[4-(1-pyrrolidinyl)-2-butynyl]-3-pyrrolidinyl]ethanethioic acid ester | 4 | 70 |
| (S)-3-Mercapto-1-[4-(1-pyrrolidinyl)-2-butynyl]-2-pyrrolidinone, monohydrochloride | 2 | 48 |

Those compounds which have $^3$H-CD IC$_{50}$ values of <1000 nM and/or $^3$H-QNB IC$_{50}$ values of <1000 uM are considered active. Those substituents which show weak activity or are inactive by these criteria may be considered pro-drugs for the more active substituents, for example: (R)-4-(Acetyloxy)-1-[4-(1-pyrrolidinyl)-2-butynyl]-2-pyrrolidinone may be a pro-drug form of (R)-4-Hydroxy-1-[4-(1-pyrrolidinyl)-2-butynyl]-2-pyrrolidinone.

The pharmaceutical preparations of the present invention may contain, for example, from about 0.5% up to about 90% of the active ingredient in combination with the carrier, more usually between 5% and 60% by weight.

The effective dosage of active ingredient employed may vary with the particular compound employed, the mode of administration, and the severity of the condition being treated. In general, however, satisfactory results are obtained when the compounds of the invention are administered at a daily dosage of from about 0.02 mg to about 100 mg/kg of patient body weight, preferably given in divided doses two to four times a day, or in sustained release form. For most patients, the total daily dosage is from about 1 mg to about 5,000 mg, preferably from about 1 mg to 20 mg. Dosage forms suitable for internal use comprise from about 0.25 to 5.0 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

A decided practical advantage is that these active compounds may be administered orally as well as by intravenous, intramuscular, or subcutaneous routes if necessary. Solid carriers include starch, lactose, dicalcium phosphate, microcrystalline cellulose, sucrose, and kaolin, while liquid carriers include sterile water, polyethylene glycols, non-ionic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, and antioxidants, e.g., vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under the conditions or manufacture and storage and must be preserved against the contaminating action of microorganisms such as bacteria and fungi. The carrier can be a solvent or dispersion medium containing, for example, water ethanol, polyol (e.g., glycerol, propylene glycol, and liquid polyethylene glycol), suitable mixtures thereof, and vegetable oils.

As used herein, "pharmaceutically acceptable carrier "includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

(S)-4-(Acetyloxy)-1-(2-propynyl)-2-pyrrolidinone

The compounds (S)-3-hydroxy-4-[[(4-methylphenyl)-sulfonyl]oxy]butanoic acid methyl ester, (S)-3-hydroxy-4-iodobutanoic acid ethyl ester, and (S)-oxiraneacetic acid ethyl ester were prepared from (S)-malic acid using literature procedures of S. Saito, et. al., Chem. Lett. 1389 (1984) and M. Larcheveque, et. al., Tetrahedron Lett., 1781, 28, (1987). These esters were individually reacted with propargylamine in methanol in the presence of sodium carbonate, under argon. The mixtures were heated at reflux overnight, then cooled in an ice bath, filtered and concentrated in vacuo. The resulting suspensions were diluted with ether, filtered and concentrated in vacuo. Toluene was added and the resulting solutions were concentrated in vacuo. The residual oils were purified by chromatography (silica gel) and the resulting solids purified by chromatography (silica gel), giving in each instance, (S)-4-hydroxy-1-(2-propynyl)-2-pyrrolidinone $[\alpha]_D^{26°} = -29°$ (dichloromethane); mp 91°–92° C.

A mixture of 6.0 g of (S)-4-hydroxy-1-(2-propynyl)-2-pyrrolidinone, 60 ml of dichloromethane, 6.55 ml of pyridine, 0.21 g of dimethylaminopyridine and 8.8 g of acetic anhydride was stirred for 2 hours, then 25 ml of methanol was added and the mixture stirred for 15 minutes. The solution was washed with 100 ml of 2N hydrochloric acid. The acid wash was extracted with 100 ml of dichloromethane and then with 100 ml of ethyl acetate. These extracts were combined with the main portion. The organic solution was washed with diluted aqueous sodium bicarbonate, dried, filtered and concentrated in vacuo. The residual oil was dissolved in dichloromethane, filtered, concentrated and crystallized from dichloromethane/ether/petroleum ether, giving 6.52 g of the desired intermediate as yellow crystals, $[\alpha]_D^{26°} = -38°$ (dichloromethane); mp 46°–47° C.

Following the same series of reactions described in Example 1, but using (R)-malic acid, the compound (R)-4-(acetyloxy)-1-(2-propynyl)-2-pyrrolidinone was prepared; $[\alpha]_D^{26°} = +38°$ (dichloromethane); mp 46.5°–47.5° C.

EXAMPLE 2

(S)-4-(Acetyloxy)-1-[4-(1-piperidinyl)-2-butynyl]-2-pyrrolidinone

A mixture of 1.5 g of (S)-4-(acetyloxy)-1-(2-propynyl)-2-pyrrolidinone, 20 ml of dry dioxane, 1.64 ml of piperidine, 0.66 g of paraformaldehyde, 3.0 ml of acetic acid and 42 mg of cupric chloride was stirred for 30 minutes and then heated at reflux for 45 minutes. The mixture was basified to pH 10 with ammonium hydroxide and then extracted with 5×50 ml of dichloromethane. The extracts were combined, dried, filtered and concentrated with toluene in vacuo. The residual oil was chromatographed on deactivated alumina, giving 2.3 g of the desired product as a pale yellow oil $[\alpha]_D^{26°} = -17°$ (dichloromethane).

Following the general procedure of Example 2, and using (S) or (R)-4-acetyloxy-1-(2-propynyl)-2-pyrrolidinone and piperidine, pyrrolidine or dimethylamine, the products of Examples 3–7, found in Table II, were prepared.

TABLE II

| Example | Isomer | Reactant | Product | $[\alpha]_D^{26°}$ (dichloromethane) |
|---|---|---|---|---|
| 3 | (S) | Pyrrolidine | (S)-4-(Acetyloxy)-1-[4-(1-pyrrolidinyl)-2-butynyl]-2-pyrrolidinone | = −16° |
| 4 | (S) | Dimethylamine | (S)-4-(Acetyloxy)-1-[4-(dimethylamino)-2-butynyl]-2-pyrrolidinone | = −22° |
| 5 | (R) | Pyrrolidine | (R)-4-(Acetyloxy)-1-[4-(1-pyrrolidinyl)-2-butynyl]-2-pyrrolidinone | = +18° |
| 6 | (R) | Piperidine | (R)-4-(Acetyloxy)-[4-(1-piperidinyl)-2-butynyl]-2-pyrrolidinone | = +17° |
| 7 | (R) | Dimethylamine | (R)-4-(Acetyloxy-1-[4-(1-dimethylamino)-2-butynyl]-2-pyrrolidinone | = +21° |

EXAMPLE 8

(S)-4-Hydroxy-1-[4-(1-piperidinyl)-2-butynyl]-2-pyrrolidinone

A mixture of 1.0 g of (S)-4-(acetyloxy)-1-[4-(1-piperidinyl)-2-butynyl]-2-pyrrolidinone, 0.75 g of sodium carbonate and 40 ml of methanol was stirred overnight, then filtered and concentrated. The residue was concentrated from dichloromethane and purified by chromatography on deactivated alumina, giving 0.83 g of the desired product as a yellow oil $[\alpha]_D^{26°} = -8°$ (c, 1.018, dichloromethane).

Following the general procedure of Example 8, and using the products of Examples 3, 4, 5, 6 and 7 as starting materials, the products of Examples 9–13, found in Table III were prepared.

TABLE III

| Example | Starting Material | Product | $[\alpha]_D^{26°}$ (dichloromethane) |
|---|---|---|---|
| 9 | Ex. 4 | (S)-1-[4-(Dimethylamino)-2-butynyl]-4-hydroxy-2-oxazolidinone | −7° |
| 10 | Ex. 5 | (R)-4-Hydroxy-1-[4-(1-pyrrolidinyl)-2-butynyl]-2-pyrrolidinone | = +7° |
| 11 | Ex. 6 | (R)-4-Hydroxy-1-[4-(1-piperidinyl)-2-butynyl]-2-pyrrolidinone | = +8° |
| 12 | Ex. 7 | (R)-1-[4-(Dimethylamino)-2-butynyl]-4-hydroxy-2-pyrrolidinone | = +8° |
| 13 | Ex. 3 | (S)-4-Hydroxy-1-[4-(1-pyrroli- | = −12° |

TABLE III-continued

| Example | Starting Material | Product | $[\alpha]_D^{26°}$ (dicloromethane) |
|---|---|---|---|
| | | dinyl)-2-butynyl]-2-pyrrolidinone | |

EXAMPLE 14

(S)-3-(Acetyloxy)-1-[4-(1-pyrrolidinyl)-2-butynyl]-2-pyrrolidinone

A mixture of 60 g of (S)-malic acid, 200 ml of dimethoxypropane and 0.5 g of 4-methylphenyl sulfonic acid was stirred for 30 minutes. Water was added and the mixture was extracted four times with dichloromethane. The extracts were combined, dried and concentrated, giving 48.6 g of solid (mp 107°-109° C.).

This solid was dissolved in 700 ml of tetrahydrofuran, cooled to −20° C. and 160 ml of a 2.0M solution of borane methyl sulfide complex in tetrahydrofuran was added dropwise. When the addition was complete the mixture was warmed to room temperature, heated at reflux for 1 hour, and cooled. Methanol was added and the mixture concentrated in vacuo. The residue was concentrated twice from 500 ml of methanol and once from 200 ml of toluene. The residue was diluted with dichloromethane, filtered and concentrated to 200 ml. Trifluoroacetic acid (20 ml) was added and this mixture was stirred overnight. The mixture was evaporated from three 200 ml portions of toluene. The residue was distilled at 1.0 mm, 100° C., giving 27 g of (S)-dihydro-3-hydroxy-2(3H)-furanone as a colorless oil.

A 100 g portion of iodotrimethylsilane was added to a solution of 37.7 g of (S)-dihydro-3-hydroxy-2(3H)-furanone in 600 ml of absolute ethanol cooled to −20° C. The mixture was allowed to warm to room temperature, then heated at reflux for 3 hours, cooled and stirred overnight. The solvent was removed in vacuo. The residue was dissolved in dichloromethane and washed with aqueous sodium thiosulfate solution and water. The dichloromethane solution was dried, concentrated in vacuo and the residue was purified by chromatography (silica gel), giving 38.0 g of solid. $[\alpha]_D^{26°} = -5°$ (dichloromethane); mp 40°-41° C.

A solution of the above solid in methanol was added dropwise to an equimolar amount of propargylamine and sodium carbonate in 500 ml of methanol. The mixture was stirred at room temperature for 1.5 hours, then heated at reflux overnight. Ether was added, the mixture was filtered and the filtrate concentrated to an oil. The oil was concentrated from toluene and then chromatographed (silica gel), giving 25 g of (S)-3-hydroxy-1-(2-propynyl)-2-pyrrolidinone $[\alpha]_D^{26°} = -99°$ (dichloromethane); mp 89°-90° C.

A mixture of 5.0 g of (S)-3-hydroxy-1-(2-propynyl)-2-pyrrolidinone, 6.7 ml of pyridine, 0.2 g of dimethylaminopyridine and 6.7 ml of acetic anhydride was stirred in a water bath for 3 hours. The mixture was diluted with 150 ml of dichloromethane, washed in succesion with water, sodium bicarbonate solution, 1N hydrochloric acid, sodium bicarbonate solution and brine, dried and concentrated, giving 6.4 g of (S)-3-(acetyloxy)-1-(2-propynyl)-2-pyrrolidinone $[\alpha]_D^{26°} = -45°$ (dichloromethane).

Following the above series of reactions, but using (R)-malic acid, the compound (R)-3-(acetyloxy)-1-(2-propynyl)-2-pyrrolidinone may be prepared.

The compound (S)-3-(acetyloxy)-1-(2-propynyl)-2-pyrrolidinone was reacted as described in Example 2 with the substitution of pyrrolidine for piperidine, giving the desired product as an amber oil $[\alpha]_D^{26°} = -29°$ (dichloro-methane).

Following the procedure of Example 14, and reacting (S) or (R)-3-(acetyloxy)-1-(2-propynyl)-2-pyrrolidinone with piperidine, pyrrolidine, or dimethylamine, the products of Examples 15–19, found in Table IV, were or can be prepared.

TABLE IV

| Example | Isomer | Reactant | Product | $[\alpha]_D^{26°}$ (dichloromethane) |
|---|---|---|---|---|
| 15 | (R) | Pyrrolidine | (R)-3-(Acetyloxy)-1-[4-(1-pyrrolidinyl)-2-butynyl]-2-pyrrolidinone | +27° |
| 16 | (S) | Dimethylamine | (S)-3-(Acetyloxy)-1-[4-(dimethylamino)-2-butynyl]-2-pyrrolidinone | −32° |
| 17 | (R) | Dimethylamine | (R)-3-(Acetyloxy)-1-[4-(dimethylamino)-2-butynyl]-2-pyrrolidine | +32° |
| 18 | (S) | Piperidine | (S)-3-(Acetyloxy)-1-[4-(1-piperidinyl)-2-butynyl]-2-pyrrolidinone | −25° |
| 19 | (R) | Piperidine | (R)-3-(Acetyloxy)-1-[4-(1-piperidinyl)-2-butynyl]-2-pyrrolidinone | +26° |

EXAMPLE 20

(S)-3-[[(1,1-Dimethylethyl)dimethylsilyl]oxy-1-[4-(1-pyrrolidinyl)-2-butynyl]-2-pyrrolidinone A mixture of 60 g of (S)-malic acid, 200 ml of dimethoxypropane and 0.5 g of p-toluenesulfonic acid was stirred until solution was complete. A 600 ml portion of water was added and the aqueous solution was extracted with six 150 ml portions of dichloromethane. The extracts were combined, washed with 150 ml of brine, dried and concentrated to dryness in vacuo. The residue was crystallized from ether, giving 48.1 g of (S)-2,2-dimethyl-4-(2-hydroxymethyl)-5-oxo-1,3-dioxolane as a white solid (mp 107°-109° C).

The above 48.1 g of white solid was dissolved in 700 ml of dry tetrahydrofuran and cooled to −25° C. A 160 ml portion of 2.0M borane methyl sulfide complex in tetrahydrofuran was added dropwise over 5 minutes. When addition was complete the mixture was stirred at room temperature for 1 hour, then at reflux for 1 hour and cooled. Methanol (100 ml) was added dropwise and the mixture was concentrated in vacuo. The residue was concentrated from 1×300 and 2×500 ml of methanol, dissolved in dichloromethane, filtered and concentrated. The resulting 44.4 g of a colorless oil was dissolved in 500 ml of dry tetrahydrofuran and cooled to 0° C. A solution of hydrazoic acid in dichloromethane (prepared by adding dropwise 10 ml of sulfuric acid to 26 g of sodium azide in 25 ml of water and 200 ml of dichloromethane at 0°-10° C., then decanting the organic solution and drying over sodium sulfate) was added to the above tetrahydrofuran solution of the alcohol. A 75 g portion of triphenylphosphine was added with stirring followed by the dropwise addition of a solution of 51 g of diethyl azodicarboxylate in 100 ml of tetrahydrofuran. The reaction was allowed to warm to room temperature, stirred overnight and the solvent removed in vacuo. The residue was dissolved in ether, filtered and concentrated in vacuo. The residue was purified by chromatography (silica gel), giving 30 g of the corresponding azide.

A mixture of 10 g of the above azide, 1.0 g of platinum oxide and 125 ml of tetrahydrofuran was hydrogenated at 40 psi for 24 hours. The catalyst was removed by filtration and the filtrate was concentrated in vacuo. The residue was triturated with ether, giving 4.2 g of (S)-3-hydroxy-2-pyrrolidinone $[\alpha]_D^{26°} = -122°$ (dichloromethane); mp 96°-97° C.

A mixture of 14 g of (S)-3-hydroxy-2-pyrrolidinone, 45 g of tert-butyldimethylsilyl chloride, 50 ml of triethylamine and 500 ml of dichloromethane was stirred overnight. The solution was washed four times with water, once with brine, dried and concentrated in vacuo. The residue was dissolved in 500 ml of methanol, refluxed overnight and concentrated in vacuo. The residue was purified by chromatography (silica gel), giving 21.5 g of (S)-3-[[(1,1-dimethylethyl)dimethylsilyl]oxy]-2-pyrrolidinone; $[\alpha]_D^{26°} = -52°$ (dichloromethane); mp 48°-49° C.

A solution of 11.5 g of potassium tert-butoxide in 300 ml of dimethylformamide was cooled to −20° C. An 18 g portion of (S)-3-[[(1,1-dimethylethyl)dimethylsilyl]oxy]-2-pyrrolidinone was added and the mixture stirred at −20° C. for 30 minutes. A 12 ml portion of 80% propargyl bromide in toluene was added and the reaction was allowed to warm to room temperature and was stirred for 1 hour. Water was added and the mixture was extracted with 5×100 ml of ether and 3×100 ml of dichloromethane. The extracts were combined, back-washed with water, dried and concentrated in vacuo, giving 15.8 g of (S)-3-[[(1,1-dimethylethyl)dimethylsilyl]oxy]-1-(2-propynyl)-2-pyrrolidinone $[\alpha]_D^{26°} = -44°$ (dichloromethane); mp 35°-36° C.

Reaction of (R)-malic acid in the above procedure will result in (R)-3-[[(1,1-dimethylethyl)dimethylsilyl]oxy]-1-(2-propynyl)-2-pyrrolidinone $[\alpha]_D^{26°} = +45°$ (dichloro-methane).

A 9.7 g portion of (S)-3-[[(1,1-dimethylethyl)-dimethylsilyl]oxy]-1-(2-propynyl)-2-pyrrolidinone and 4.8 g of pyrrolidine were reacted as described in Example 2 with the substitution of piperidine with pyrrolidine, giving 6.4 g of the desired product as a pale yellow oil, $[\alpha]_D^{26°} = -35°$ (dichloromethane).

Following the procedure of Example 20, but reacting (S)- or (R)-3-[[(1,1-dimethylethyl)dimethylsilyl)oxy]-1-(2-propynyl)-2-pyrrolidinone with piperidine, pyrrolidine or dimethylamine, the products of Examples 21-25, found in Table V, were or can be prepared.

TABLE V

| Example | Isomer | Reactant | Product | $[\alpha]_D^{26°}$ | mp |
|---|---|---|---|---|---|
| 21 | (S) | Piperidine | (S)-3-[[(1,1-Dimethylethyl)dimethylsilyl]oxy]-1-[4-(1-piperidinyl)-2-butynyl]-2-pyrrolidinone | −32° | |
| 22 | (S) | Dimethylamine | (S)-1-[4-(Dimethylamino)-2-butynyl]-3-[(1,1-dimethylethyl)dimethylsilyl]oxy]-2-pyrrolidinone | −37° | 34-35° C. |
| 23 | (R) | Pyrrolidine | (R)-3-[[(1,1-Dimethylethyl)dimethylsilyl]oxy]-1-[4-(1-pyrrolidinyl)-2-butynyl]-2-pyrrolidinone | | |
| 24 | (R) | Piperidine | (R)-3-[[(1,1-Dimethylethyl)dimethylsilyl]oxy]-1-[4-(1-piperidinyl)-2-butynyl]-2-pyrrolidinone | | |
| 25 | (R) | Dimethylamine | (R)-1-[4-(Dimethylamino)-2-butynyl]-3-[[(1,1-dimethylethyl)dimethylsilyl]oxy]-2-pyrrolidinone | | |

EXAMPLE 26

(S)-3-Hydroxy-1-[4-(1-pyrrolidinyl)-2-butynyl]-2-pyrrolidinone

Method A

A 3.0 g portion of (S)-3-[[(1,1-dimethylethyl)dimethylsilyl]oxy]-1-[4(1-pyrrolidinyl)-2-butynyl]-2-pyrrolidinone was dissolved in 50 ml of methanolic hydrogen chloride and 5 ml of water and stirred for 3 hours. The solvent was removed at reduced pressure, the residue was washed three times with ether, then basified with ammonium hydroxide. The resulting aqueous mixture was extracted five times with tetrahydrofuran, dried and concentrated, giving 0.7 g of the desired product as a white solid, $[\alpha]_D^{26°} = -63°$ (dichloromethane); mp 81°-82° C.

Method B

A 10 g portion of (S)-3-(acetyloxy)-1-[4-(1-pyrrolidinyl)-2-butynyl]-2-pyrrolidinone in 250 ml of methanol containing 8.0 g of sodium carbonate was stirred for 4 hours. The resulting mixture was diluted with dichloromethane and filtered. The filtrate was concentrated and the residue purified by chromatography (alumina), giving 5.45 g of the desired product as a colorless solid, mp 79°-81° C.

Using the products of Examples 21-25 and the above method A, or the products of Examples 15-19 and the above method B, the products of Examples 27-31, found in Table VI, were or can be prepared.

TABLE VI

| Example | Starting Material (Example) | Method | Product | $[\alpha]_D^{26°}$ (dichloromethane) | mp |
|---|---|---|---|---|---|
| 27 | 21 | A | (S)-3-Hydroxy-1-[4-(1-piperidinyl)-2-butynyl]- | = −60° | 79-80° C. |

TABLE VI-continued

| Example | Starting Material (Example) | Method | Product | $[\alpha]_D^{26°}$ (dichloromethane) | mp |
|---|---|---|---|---|---|
|  | 18 | B |  2-pyrrolidinone |  |  |
| 28 | 22 | A | (S)-1-[4-(Dimethylamino)-2-butynyl]-3-hydroxy- | = −71° |  |
|  | 16 | B | 2-pyrrolidinone |  |  |
| 29 | 23 | A | (R)-3-Hydroxy-1-[4-(1-pyrrolidinyl)-2-butynyl]-2-pyrrolidinone | = +60° | 81–85° C. |
|  | 15 | B |  |  |  |
| 30 | 24 | A | (R)-3-Hydroxy-1-[4-(1-piperidinyl)-2-butynyl]- | = +59° | 76–77° C. |
|  | 19 | B | 2-pyrrolidinone |  |  |
| 31 | 25 | A | (R)-1-[4-(Dimethylamino-2-butynyl]-3-hydroxy- | = +61° |  |
|  | 17 | B | 2-pyrrolidinone |  |  |

EXAMPLE 32

(R)-3-(Acetyloxy)-1-[4-(1-pyrrolidinyl)-2-butynyl]-2-pyrrolidinone

A solution of 0.5 g of (S)-3-hydroxy-1-[4-(1-pyrrolidinyl)-2-butynyl]-2-pyrrolidinone, 0.75 g of triphenylphosphine and 0.2 ml of acetic acid in 20 ml of tetrahydrofuran was stirred at room temperature in a tap water bath. A 0.6 g portion of diethyl azodicarboxylate was added dropwise, this mixture was stirred overnight, then the solvent was removed in vacuo. The residue was purified by chromatography (silica gel), giving 0.4 g of the desired product.

This alternate procedure may be used to convert the products of Examples 27–31 to the products of Examples 14, 16–19.

EXAMPLE 33

(S)-3-(Acetyloxy)-1-[4-(1-pyrrolidinyl)-2-butynyl]-2-pyrrolidinone

A solution of 0.4 g of (S)-3-hydroxy-1-[4-(1-pyrrolidinyl)-2-butynyl]-2-pyrrolidinone and 1.0 ml of acetic anhydride in 20 ml of dichloromethane was stirred overnight. The solvent was removed in vacuo. The residue was basified with potassium bicarbonate solution and extracted with dichloromethane. The dichloromethane solution was washed with water, dried, concentrated in vacuo and the residue was purified by chromatography (alumina), giving the desired product.

Following the procedure of this example, using the products of Examples 27–31, the products of Examples 15–19 may be derived.

EXAMPLE 34

(R)-3-[(4-Nitrobenzoyl)oxy]-1-[4-(1-pyrrolidinyl)-2-butynyl]-2-pyrrolidinone

A solution of 0.9 g of diethyl azodicarboxylate in 5 ml of tetrahydrofuran was added dropwise to a solution of 0.9 g of (S)-3-hydroxy-1-[4-(1-pyrrolidinyl)-2-butynyl]-2-pyrrolidinone, 1.1 g of triphenylphosphine and 0.9 g of 4-nitrobenzoic acid in 30 ml of dry tetrahydrofuran. The mixture was stirred overnight and the solvent was removed in vacuo. The residue was purified by chromatography (silica gel), giving 1.2 g of the desired product as off white crystals, $[\alpha]_D^{26°} = +41°$ (dichloromethane); mp 89°–90° C.

Following the general procedure of Example 34, using the products of Examples 27–31, the products of Examples 35–39, found in Table VII, were or can be prepared.

TABLE VII

| Example | Starting Material (Example) | Product | $[\alpha]_D^{26°}$ (dichloromethane) | mp |
|---|---|---|---|---|
| 35 | 29 | (S)-3-[(4-Nitrobenzoyl)oxy]-1-[4-(1-pyrrolidinyl)-2-butynyl]-2-pyrrolidinone |  |  |
| 36 | 30 | (S)-3-[(4-Nitrobenzoyl)oxy]-1-[4-(1-piperidinyl)-2-butynyl]-2-pyrrolidinone |  |  |
| 37 | 27 | (R)-3-[(4-Nitrobenzoyl)oxy]-1-[4-(1-piperidinyl)-2-butynyl]-2-pyrrolidinone | +43° | 86–87° C. |
| 38 | 28 | (R)-1-[4-(Dimethylamino)-2-butynyl]-3-[(4-nitrobenzoyl)oxy]-2-pyrrolidinone | +46° | 70–71° C. |
| 39 | 31 | (S)-1-[4-(Dimethylamino)-2-butynyl]-3-[(4-nitrobenzoyl)oxy]-2-pyrrolidinone |  |  |

EXAMPLE 40

(R)-3-Hydroxy-1-[4-(1-pyrrolidinyl)-2-butynyl]-2-pyrrolidinone

A mixture of 1.6 g of (R)-3-[(4-Nitrobenzoyl)oxy]-1-[4-(1-pyrrolidinyl)-2-butynyl]-2-pyrrolidinone, 1.6 g of potassium carbonate and 60 ml of methanol was stirred for 2 hours, diluted with dichloromethane and filtered. The filtrate was concentrated to dryness. The residue was chromatographed (alumina) to give 0.8 g of the desired product as an off white solid; mp 81°–85° C.

Using the above procedure the products of Examples 35–39 may be converted to the products of Examples 26, 27, 28, 30 and 31.

EXAMPLE 41

(S)-3-[[(1,1-Dimethylethyl)dimethylsilyl]oxy]-1-[4-(1-piperidinyl)-2-butynyl]-2-pyrrolidinone In one portion, 11.6 g of (S)-3-[[(1,1-dimethyl-ethyl)dimethylsilyl]oxy]-2-pyrrolidinone was added to a suspension of 2.35 g of 60% sodium hydride in mineral oil in 400 ml of tetrahydrofuran which was cooled to 0° C. The resulting solution was stirred at room temperature until solution was complete, then recooled to 0° C. An 80% solution of propargyl bromide in toluene (8.5 ml) was added and the resulting solution was stirred overnight. The solution was diluted with dichloromethane, washed with water, dried and concentrated in vacuo. The residue was purified by chromatography (silica gel), giving (S)-3-[[(1,1-dimethylethyl)-dimethylsilyl]oxy]-1-(2-propynyl)-2-pyrrolidinone, $[\alpha]_D^{26}= -44°$ (dichloromethane); mp 35°-36° C.

A mixture 9.7 g of (S)-3-[[(1,1-dimethylethyl)-dimethylsilyl]oxy]-1-(2-propynyl)-2-pyrrolidinone, 50 ml of dioxane, 5.7 g of piperidine, 1.8 g of paraformaldehyde, 10.5 ml of acetic acid and 0.16 g of cupric chloride was stirred for 30 minutes and then refluxed for 2 hours. The mixture was cooled in an ice bath, basified with ammonium hydroxide and diluted with water and dichloromethane. The dichloromethane solution was washed with water, dried and concentrated in vacuo, giving the desired product as an oil, $[\alpha]_D^{26}= -32°$ (dichloromethane).

As an alternate procedure, the compounds of Example 20 and 22-25 may be prepared by reacting (S)-or (R)-3-[[(dimethylethyl)dimethyl-silyl]oxy]-2-pyrrolidinone in the above procedure and using pyrrolidine, piperidine or dimethylamine where piperidine is described.

EXAMPLE 42

(S)-3-Hydroxypyrrolidine

A 1.0 g portion of lithium aluminum hydride was added under nitrogen to a stirred solution of 2.75 g of (S)-3-[[(dimethylethyl)dimethylsilyl]oxy]-2-pyrrolidinone in 50 ml of dry tetrahydrofuran at 0° C. The mixture was heated at reflux for 4 hours, cooled to 0° C. and then treated sequentially with 1 ml of water, 1 ml of 15% sodium hydroxide and 2 ml of water. The mixture was diluted with 360 ml of ether, filtered and the cake washed with dichloromethane. The filtrate and wash were combined, dried and concentrated to give (S)-3-hydroxypyrrolidine as a colorless oil.

EXAMPLE 43

(S)-1-[4-[3-(Acetyloxy)-1-pyrrolidinyl]-2-butynyl]-2-pyrrolidinone

A 0.5 g portion of (S)-3-hydroxypyrrolidine, as described in Example 42, was reconcentrated twice from toluene, dissolved in 80 ml of dichloromethane and cooled to 0° C. A 3.8 ml portion of triethylamine and 2.8 ml of benzylchloroformate were added with stirring. The reaction was stirred overnight, diluted with 300 ml of dichloromethane and extracted with 80 ml of 5% hydrochloric acid and 5% sodium bicarbonate solution. The aqueous phases were combined, saturated with sodium chloride and extracted with 3×150 ml of ethyl acetate. The organic phases were combined, dried, filtered and concentrated in vacuo. The residue was purified by chromatography (alumina) giving 940 g of (S)-3-hydroxy-1-pyrrolidinecarboxylic acid, phenylmethyl ester as a yellow oil $[\alpha]_D^{26}= +21°$ (c, 1.054 methanol).

A mixture of 2.87 g of (S)-3-hydroxy-1-pyrrolidinecarboxylic acid, phenylmethyl ester, 2.0 ml of acetic anhydride, 2.0 ml of pyridine and 20 mg of 4-dimethylaminopyridine in 25 ml of dichloromethane was stirred for 72 hours. Methanol (2 ml) and dichloromethane (50 ml) were added. The dichloromethane solution was washed with 40 ml each of 1N hydrochloric acid and 5% sodium bicarbonate solution, dried, filtered and concentrated in vacuo. The residue was purified by chromatography (silica gel), giving 3.1 g of (S)-3-(acetyloxy)-1-pyrrolidinecarboxylic acid, phenylmethyl ester as a colorless oil, $[\alpha]_D^{26}= +17°$ (dichloromethane).

A 2.3 g portion of (S)-3-(acetyloxy)-1-pyrrolidimecarboxylic acid, phenylmethyl ester and 200 mg of 10% palladium on carbon in 75 ml of methanol was stirred under an atmosphere of hydrogen for 2 hours. The reaction was degassed with argon, filtered and the catalyst washed with dichloromethane. The filtrate and wash were combined ad concentrated, giving 1.03 g of 3-acetoxypyrrolidine.

A mixture of 500 mg of (S)-3-acetoxypyrrolidine, 530 mg of N-propargyl-2-pyrrolidinone, 150 mg of paraformaldehyde and 50 mg of cupric chloride in 10 ml of dioxane was stirred at reflux under argon for 4 hours. The dioxane was evaporated, the residue was treated with 5 ml of 1N hydrochloric acid and extracted twice with ether. The aqueous acid was basified with 1 g of sodium bicarbonate and extracted twice with dichloromethane. The extracts were combined, dried, filtered and concentrated in vacuo to an oil. This oil was purified by chromatography (alumina), giving 490 mg of the desired product as a yellow oil, $[\alpha]_D^{26}= -3°$ (c, 1.02, methanol).

Following the general procedure of Example 43 and using (R)-3-hydroxy pyrrolidine [M. Hashimoto et. al., Chem. Lett., 893 (1986)] or commercially available (racemic)-3-hydroxy pyrrolidine, the products of Examples 44 and 45 found in Table VIII can be obtained.

TABLE VIII

| Example | Starting Material | Product | $[\alpha]_D^{26°}$ (dichloromethane) |
|---|---|---|---|
| 44 | (R)-3-Hydroxy pyrrolidine | (R)-1-[4-[3-(Acetyloxy)-1-pyrrolidinyl]-2-butynyl]-2-pyrrolidinone | +3° |
| 45 | (racemic)-3-Hydroxy pyrrolidine | (racemic)-1-[4-[3-(Acetyloxy)-1-pyrrolidinyl]-2-butynyl]-2-pyrrolidinone | |

EXAMPLE 46

(Racemic)-1-[4-(3-Hydroxy-1-pyrrolidinyl)-2-butynyl]-2-pyrrolidinone

A mixture of 800 mg of (racemic)-1-[4-[3-(acetyloxy)-1-pyrrolidinyl]-2-butynyl]-2-pyrrolidinone, 595 mg of sodium carbonate and 40 ml of methanol was stirred overnight. An equal volume of dichloromethane was added and this mixture was filtered. The filtrate was concentrated and the residue was diluted with dichloromethane, filtered and concentrated in vacuo. The residue was purified by chromatography (alumina), giving 470 mg of the desired product as a pale yellow oil.

Following the procedure of Example 46, the (S) or (R) isomers of the desired product were prepared from (S) or (R)-1-[4-[3-(acetyloxy)-1-pyrrolidinyl]-2-butynyl]-2-pyrrolidinone.

EXAMPLE 47

(Racemic)-N-[4-[3-(Acetyloxy)-1-pyrrolidinyl]-2-butynyl]-N-methyl acetamide

A mixture of 1.17 g of 3-acetoxy pyrrolidine, 1.2 g of N-methyl-N-propargyl acetamide, 465 mg of paraformaldehyde, 200 mg of cuprous chloride, 1.5 ml of acetic acid and 50 ml of dioxane was stirred at reflux under argon for 75 minutes. A 100 ml portion of dichloromethane was added followed by the addition of 50 ml of 10% aqueous sodium bicarbonate. The phases were separated, sodium chloride was added to the aqueous phase and the aqueous phase was reextracted with dichloromethane. The organic solutions were combined, dried, filtered and concentrated. The residue was purified by chromatography (alumina), giving 1.43 g of the desired product as a yellow oil.

EXAMPLE 48

(Racemic)-N-[4-(3-Hydroxy-1-pyrrolidinyl)-2-butynyl]-N-methyl acetamide

A mixture of 820 mg of (racemic)-N-[4-[3-(acetyloxy)-1-pyrrolidinyl]-2-butynyl]-N-methyl acetamide, 635 mg of sodium carbonate and 40 ml of methanol was stirred overnight. An equal volume of dichloromethane was added, the mixture filtered and the solvents concentrated. This residue was purified by chromatography (alumina), giving 500 mg of the desired product as a yellow oil.

EXAMPLE 49

(Racemic)-1-[4-(3-Methoxy-1-pyrrolidinyl)-2-butynyl]-2-pyrrolidinone

A solution of 35.6 ml of benzylchloroformate in 200 ml of dichloromethane was added dropwise to a mixture of 10 g of (racemic)-3-pyrrolidinol, 48.3 ml of triethylamine and 725 ml of dichloromethane which was cooled to 0° C. The mixture was stirred for 48 hours at room temperature. The dichloromethane solution was extracted with 5% hydrochloric acid and 5% aqueous sodium bicarbonate. The acid and bicarbonate washes were combined, salted with sodium chloride and extracted with 2×750 ml of ethyl acetate. The combined organic extracts were dried and concentrated, giving 22.7 g of (racemic)-N-carbobenzyloxy-3-pyrrolidinol. A mixture of 2.5 g of (racemic)-N-carbobenzyloxy-3-pyrrolidinol, 2.0 ml of methyl iodide and 5.1 g of silver oxide in 50 ml of dimethylformamide was stirred at room temperature for 2 days. The mixture was diluted with ether and then filtered. The filtrate was concentrated to a small volume. The ether solution was washed with water, dried and concentrated to dryness in vacuo. The residue was purified by chromatography (silica gel) to give 2.4 g of (racemic)-N-carbobenzyloxy-3-methoxypyrrolidine as a pale yellow oil.

A 2.1 g portion of (racemic)-N-carbobenzyloxy-3-methoxypyrrolidine in 80 ml of methanol containing palladium on carbon was stirred under an atmosphere of hydrogen for 2 hours. The mixture was filtered and the cataylst washed with dichloromethane. The combined filtrate and wash were concentrated in vacuo, giving 730 mg of (racemic)-3-methoxypyrrolidine.

A mixture of 365 mg of (racemic)-3-methoxypyrrolidine, 530 mg of N-propargyl-2-pyrrolidinone, 180 mg of paraformaldehyde, 0.6 ml of acetic acid, 20 ml of dioxane and 10 mg of cuprous chloride was stirred at reflux under argon for 1 hour. The reaction was cooled and treated with a mixture of 3 ml of 5N sodium hydroxide and 2 ml of water. The mixture was extracted twice with dichloromethane. The extracts were combined, dried, filtered and concentrated in vacuo to an oil. The oil was purified by chromatography (alumina), giving 520 mg of the desired product as a yellow oil.

EXAMPLE 50

(Racemic)-N-[4-(3-Methoxy-1-pyrrolidinyl)-2-butynyl]-N-methyl acetamide

A 25.0 g portion of N-methyl propargylamine was added dropwise with stirring to 145 ml of acetic anhydride which was cooled to 0° C. The mixture was stirred overnight at room temperature and then concentrated in vacuo. The residue was purified by Kugelrohr distillation, giving 39.5 g of N-methyl-N-propargyl acetamide as a colorless oil, bp 50°-60° C., 0.2 mm.

A mixture of 365 mg of (racemic)-3-methoxypyrrolidine, 480 mg of N-methyl-N-propargyl acetamide, 180 mg of paraformaldehyde, 0.6 ml of acetic acid, 20 ml of dioxane and cuprous chloride catalyst was stirred at reflux under argon for 1 hour. The mixture was treated with 3 ml of 5N sodium hydroxide and 2 ml of water and extracted twice with dichloromethane. The extracts were combined, concentrated and purified by chromatography (alumina), giving 610 mg of the desired product.

Following the procedures of Examples 47-50, using the appropriate isomers as starting materials the corresponding (S) and (R) isomeric products may be obtained.

EXAMPLE 51

(S)-3-Methoxy-1-[4-(1-piperidinyl)-2-butynyl]-2-pyrrolidinone

A mixture of 2.0 g of (S)-3-hydroxy-1-(2-propynyl)-2-pyrrolidinone, 70 g of silica gel and 200 ml of dichloromethane was cooled in an ice bath. A 300 ml solution of diazomethane in ether was added portionwise. The reaction was filtered, washed with methanol and concentrated in vacuo. The residue was purified by chromatography (silica gel), giving 700 mg of (S)-3-methoxy-1-(2-propynyl)-2-pyrrolidinone, $[\alpha]_D^{26} = -71°$ (dichloromethane).

A mixture of 250 mg of (S)-3-methoxy-1-(2-propynyl)-2-pyrrolidinone, 3.0 ml of dioxane, 0.3 ml of acetic acid, 0.15 g of piperidine, 75 mg of paraformaldehyde and 10 mg of cuprous chloride was heated at reflux for 1 hour then cooled to 0° C. and basified with 1N sodium hydroxide. This mixture was extracted with dichloromethane. The dichloromethane solution was washed with brine, dried and concentrated, giving the desired product, $[\alpha]_D^{26} = -43°$ (dichloromethane).

Following the procedure of Example 51, using (S) or (R)-3-hydroxy-1-(2-propynyl)-2-pyrrolidinone and finally reacting with piperidine, pyrrolidine or dimethylamine, the compounds of Examples 52-56, found in Table IX were or can be obtained.

TABLE IX

| Example | Isomer | Reactant | Product | $[\alpha]_D^{26°}$ (dichloromethane) |
|---|---|---|---|---|
| 52 | (R) | Piperidine | (R)-3-Methoxy-1-[4-(1-piperidinyl)-2-butynyl]-2-pyrrolidinone | +44° |
| 53 | (S) | Pyrrolidine | (S)-3-Methoxy-1-[4-(1-pyrrolidinyl)-2-butynyl]-2-pyrrolidinone | −47° |
| 54 | (R) | Pyrrolidine | (R)-3-Methoxy-1-[4-(1-pyrrolidinyl)-2-butynyl]-2-pyrrolidinone | +47° |
| 55 | (S) | Dimethylamine | (S)-1-[4-(Dimethylamino)-2-butynyl]-3-methoxy-2-pyrrolidinone | |
| 56 | (R) | Dimethylamine | (R)-1-[4-(Dimethylamino)-2-butynyl]-3-methoxy-2-pyrrolidinone | |

EXAMPLE 57

(S)-S-[1-[4-(Dimethylamino)-2-butynyl]-2-oxo-3-pyrrolidinyl]ethanethioic acid ester A solution of 0.4 g of (R)-1-[4-(dimethylamino)-2-butynyl]-3-hydroxy-2-pyrrolidinone, 0.6 ml of triethylamine and 0.3 ml of methane sulfonyl chloride in 10 ml of dichloromethane was stirred at 0° C. for 1 hour. Saturated aqueous sodium carbonate was added and the mixture separated. The aqueous portion was washed with dichloromethane. The organic layer and wash were combined, washed with sodium chloride solution, dried and evaporated. The residue was evaporated from 10 ml of toluene. The residual oil was purified by chromatography (silica gel), giving 0.4 g of (R)-1-[4-(dimethylamino)-2-butynyl]-3-[(methane sulfonyl)oxy]-2-pyrrolidinone as a colorless oil.

A solution of 0.4 g of (R)-1-[4-(dimethylamino)-2-butynyl]-3-[(methane sulfonyl)oxy]-2-pyrrolidinone in 5 ml of methanol was filtered into a solution of 0.4 ml of thioacetic acid, 1.0 ml of 3.53M sodium methoxide in methanol and 5 ml of methanol. The solution was stirred overnight, then evaporated in vacuo. The residue was purified by chromatography (silica gel), giving the desired product as a pale yellow oil, $[\alpha]_D^{26} = +11°$ (methanol).

Following the procedure of Example 57, using the (S) or (R) isomers of 1-[4-(dimethylamino)-2-butynyl]-3-hydroxy-2-pyrrolidinone, 1-4-(1-pyrrolidinyl)-2-butynyl]-3-hydroxy-2-pyrrolidinone, or 1-[4-(1-piperidinyl)-2-butynyl]-3-hydroxy-2-pyrrolidinone, the compounds of Examples 58–62 found in Table X were obtained.

EXAMPLE 63

(R)-3-Mercapto-1-[4-(1-pyrrolidinyl)-2-butynyl]-2-pyrrolidinone

A solution of 1.76 g of (S)-3-hydroxy-1-[4-(1-pyrrolidinyl)-2-butynyl]-2-pyrrolidinone and 2.4 ml of triethylamine in 50 ml of dichloromethane was cooled to 0° C. A 1.2 ml portion of methane sulfonyl chloride was added dropwise and the solution was stirred at 0° C. for 1 hour. The mixture was washed with aqueous sodium bicarbonate and brine, dried, concentrated and reconcentrated from toluene. The residue was purified by chromatography (silica gel) to give 1.5 g of (S)-3-[(methanesulfonyl)oxy]-1-[4-(1-pyrrolidinyl)-2-butynyl]-2-pyrrolidinone as a colorless oil.

A solution of 1.5 g of (S)-3-[(methanesulfonyl)oxy]-1-[4-(1-pyrrolidinyl)-2-butynyl]-2-pyrrolidinone in 25 ml of methanol was filtered into a solution of 1.6 ml of thioacetic acid and 4.0 ml of 3.53M methanolic sodium methoxide in 75 ml of methanol. This mixture was stirred for 24 hours and then concentrated in vacuo. The residue was partitioned between water and dichloromethane. The organic layer was separated, washed with brine, dried and concentrated. The residue was purified by chromatography (silica gel) giving 1.8 g of (R)-S-[2-oxo-1-[4-(1-pyrrolidinyl)-2-butynyl]-3-pyrrolidinyl]ethanethioic acid ester as a pale yellow oil, $[\alpha]_D^{26} = +4°$ (dichloromethane).

A 0.8 g portion of the above ethanethioic acid ester derivative was reacted with 100 ml of 1.28M methanolic hydrochloric acid, giving the desired product as a colorless gum, $[\alpha]_D^{26} = +23°$ (methanol).

Following the procedure of Example 63, and using the compounds of Examples 26–31, the compounds of Examples 64–68 found in Table XI were prepared.

TABLE X

| Example | Isomer | Product | $[\alpha]_D^{26°}$ (dichloromethane) |
|---|---|---|---|
| 58 | (R) | (R)-S-[1-[4-(Dimethylamino)-2-butynyl]-2-oxo-3-pyrrolidinyl]-ethanethioic acid ester | −6° |
| 59 | (S) | (S)-S-[2-Oxo-1-[4-(1-piperidinyl)-2-butynyl]-3-pyrrolidinyl]ethanethioic acid ester | +5° |
| 60 | (R) | (R)-S-[2-Oxo-1-[4-(1-piperidinyl)-2-butynyl]-3-pyrrolidinyl]ethanethioic acid ester | −11° |
| 61 | (S) | (S)-S-[2-Oxo-[4-(1-pyrrolidinyl)-2-butynyl]-3-pyrrolidinyl]ethanethioic acid ester | +3° |
| 62 | (R) | (R)-S-[2-Oxo-1-[4-(1-pyrrolidinyl)-2-butynyl]-3-pyrrolidinyl]ethanethioic acid ester | −4° |

TABLE XI

| Example | Starting Material | Product | $[\alpha]_D^{26°}$ (methanol) |
|---|---|---|---|
| 64 | 25 | (S)-3-Mercapto-1-[4-(1-pyrrolidinyl)-2-butynyl]-2-pyrrolidinone, monohydrochloride | −22° |
| 65 | 26 | (S)-3-Mercapto-1-[4-(1-piperidinyl)-2-butynyl]-2-pyrrolidinone, monohydrochloride | −20° |
| 66 | 29 | (R)-3-Mercapto-1-[4-(1-piperidinyl)-2-butynyl]-2-pyrrolidinone, monohydrochloride | +24° |
| 67 | 30 | (R)-1-[4-(Dimethylamino)-2-butynyl]-3-mercapto-2-pyrrolidinone, monohydrochloride | −50° |
| 68 | 27 | (S)-1-[4-(Dimethylamino)-2-butynyl]-3-mercapto-2-pyrrolidinone, monohydrochloride | |

EXAMPLE 69

(S)-4-[[(1,1-Dimethylethyl)dimethylsilyl]oxy]-1-[4-(1-pyrrolidinyl)-2-butynyl]-2-pyrrolidinone A mixture of 25 g of (S)-4-hydroxy-1-(2-propynyl)-2-pyrrolidinone, 39.8 g of t-butyldimethylsilyl chloride and 38.5 ml of triethylamine in 200 ml of dichloromethane was stirred under argon overnight. The mixture was washed with 300 ml of water, dried and evaporated. The residual oil was purified by chromatography, (silica gel) giving 42.7 g of (S)-4-[[(1,1-dimethylethyl)dimethylsilyl]oxy]-1-(2-propynyl)-2-pyrrolidinone.

A mixture of 1.5 g of (S)-4-[[(1,1-dimethylethyl)dimethylsily]oxy]-1-(2-propynyl)-2-pyrrolidinone, 20 ml of dioxane, 0.66 ml of pyrrolidine, 0.32 g of paraformaldehyde, 3.0 ml of acetic acid and 42 mg of cuprous chloride was reacted as described in Example 1 with the substitution of dimethylamine for piperidine. The residue was purified by chromatography (alumina), giving 290 mg of the desired product as a pale yellow oil, $[\alpha]_D^{26} = +4°$ (dichloromethane).

EXAMPLE 70

(S)-4-Hydroxy-1-[4-(1-pyrrolidinyl)2-butynyl]-2-pyrrolidinone

A mixture of 7.2 g of (S)-4-[[(1,1-dimethylethyl)dimethylsilyl]oxy]-1-[4-(1-pyrrolidinyl)-2-butynyl]-2-pyrrolidinone and 75 ml of 1N methanolic hydrochloric acid was stirred for 1 hour, then cooled to 0° C. and basified to pH 8 with methanolic potassium hydroxide. The mixture was filtered and the filtrate evaporated. The residue was reevaporated from dichloromethane. The residual oil was purified by chromatography (alumina), giving 0.4 g of the desired product as a yellow oil, $[\alpha]_D^{26} = -12°$ (dichloromethane).

EXAMPLE 71

(S)-4-(3-Hydroxy-2-oxo-1-pyrrolidinoyl)N,N,N-trimethyl-2-butynyl-1-ammonium, iodide A 0.35 g portion of (S)-1-[4-(dimethylamino)-2-butynyl-3-hydroxy-2-pyrrolidinone was dissolved in dichloromethane, dried, filtered and concentrated. The residue was dissolved in a mixture of dichloromethane and ether and 0.5 ml of methyl iodide was added. The mixture was stirred for 2.5 hours and then the solid was collected and washed with dichloromethane, giving the desired compound as colorless crystals, $[\alpha]_D^{26} = -26°$ (methanol); mp 116°-117° C.

EXAMPLE 72

(R)-3-(Methyldithio)-1-[4-(1-pyrrolidinyl)-2-butynyl]-2-pyrrolidinone hydrochloride A solution of 430 mg of (R)-3-mercapto-1-[4-(1-pyrrolidinyl)-2-butynyl]-2-pyrrolidinone hydrochloride in 20 ml of dichloromethane was cooled to 0° C. in an ice bath. Successively, 50 μl of trimethylamine and 0.5 ml of methylthiomethylthiosulfate were added and the resulting solution was stirred at room temperature for 30 minutes. A 1N sodium hydroxide solution (2 ml) was added and the resulting mixture was washed with saturated aqueous sodium chloride, dried and concentrated in vacuo. The residue was purified by chromatography (alumina) and the eluent containing the product band was acidified with an excess of 1.4N methanolic hydrogen chloride to give 0.41 g of the desired compound as a pale yellow oil, $[\alpha]_D^{26} = +23°$ (methanol).

EXAMPLE 73

[R-(R*,R*)-3,3-Dithiobis[1-[4-(1-piperidinyl)]-2-butynyl]-2-pyrrolidione dihydrochloride In one portion, 90 mg of 2-pyridyldisulfide was added to a solution 230 mg of (R)-3-mercapto-1-[4-(1-pyrrolidinyl)-2-butynyl]-2-pyrrolidinone hydrochloride in 20 ml of dichloromethane. The resulting solution was stirred at room temperature for 30 minutes, washed successively with aqueous sodium carbonate and water, dried and concentrated in vacuo. The residue was purified by chromatography (alumina) and the eluent containing the product band acidified with an excess of methanolic hydrogen chloride and concentrated in vacuo to give 200 mg of the desired product as a pale yellow oil, $[\alpha]_D^{26} = +25°$ (methanol).

We claim:

1. A compound selected from those of formula;

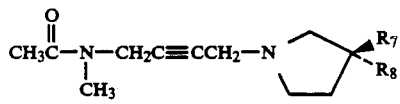

wherein $R_7$ and $R_8$ are independently selected from the group consisting of $(C_1-C_6)$acyloxy, $(C_1-C_6)$alkoxy, hydroxy, thio, $(C_1-C_6)$alkylthio, $(C_1-C_6)$alkyldithio with the proviso that one of $R_7$ and $R_8$ must be hydrogen.

2. The compound according to claim 1, (racemic)-N-[4-[3-(acetyloxy)-1-pyrrolidinyl]-2-butynyl]-N-methylacetamide.

3. The compound according to claim 1, (racemic)-N-[4-(3-hydroxy-1-pyrrolidinyl)-2-butynyl]-N-methylacetamide.

4. The compound according to claim 1, (racemic)-N-[4-(3-methoxy-1-pyrrolidinyl)-2-butynyl]-N-methylacetamide.

5. The oxidative dimers of the compounds of claim 1, wherein any one of $R_7$ or $R_8$ may be thio.

6. A method of treating central cholinergic disfunction in a mammal which comprises administering to said mammal an effective amount of a compound selected from those of claim 1.

7. A pharmaceutical composition of matter in dosage unit form comprising from about 1 to about 5000 mg of a compound of claim 1 in association with a pharmaceutically acceptable carrier.

* * * * *